(12) United States Patent
Shepard et al.

(10) Patent No.: US 6,783,834 B2
(45) Date of Patent: Aug. 31, 2004

(54) LOOP MATERIAL FOR TOUCH FASTENING

(75) Inventors: William H. Shepard, Amherst, NH (US); Paul R. Erickson, New Boston, NH (US)

(73) Assignee: Velcro Industries B.V., Curacao ( * ) Notice: Subject to any disclaimer, the term of this patent is extended or adjusted under 35 U.S.C. 154(b) by 35 days.

(21) Appl. No.: 09/996,618

(22) Filed: Nov. 27, 2001

(65) Prior Publication Data

US 2002/0037390 A1 Mar. 28, 2002

Related U.S. Application Data

(63) Continuation of application No. 09/262,159, filed on Mar. 3, 1999, now Pat. No. 6,329,016, which is a continuation-in-part of application No. PCT/US98/18401, filed on Sep. 3, 1998, which is a continuation-in-part of application No. 08/922,292, filed on Sep. 3, 1997.

(51) Int. Cl.[7] .............. D04H 11/00; D04H 11/08; B32B 5/08
(52) U.S. Cl. .............. 428/92; 428/89; 428/96; 428/99; 428/100; 442/402; 442/336; 442/352; 442/104; 442/109
(58) Field of Search .............. 428/89, 92, 99, 428/100; 442/402, 336, 352, 104, 109, 103

(56) References Cited

U.S. PATENT DOCUMENTS

| | | |
|---|---|---|
| 2,913,803 A | 11/1959 | Dodds |
| 3,341,386 A | 9/1967 | White et al. |
| 3,347,735 A | 10/1967 | Dildilian |
| 3,674,618 A | 7/1972 | Spann |
| 3,694,867 A | 10/1972 | Stumpf |
| 3,705,065 A | 12/1972 | Stumpf |
| 3,708,361 A | 1/1973 | Stumpf |
| 3,708,833 A | 1/1973 | Ribich et al. ......... 24/204 |
| 3,720,578 A | 3/1973 | Heling et al. |
| 3,756,907 A | 9/1973 | Heling |
| 3,822,162 A | 7/1974 | Stumpf |
| 4,116,892 A | 9/1978 | Schwarz |
| 4,154,885 A | 5/1979 | Tecl et al. |

(List continued on next page.)

FOREIGN PATENT DOCUMENTS

| | | |
|---|---|---|
| EP | 0 341 993 | 11/1989 |
| EP | 0 482 749 A1 | 4/1992 |
| EP | 0 604 731 A1 | 6/1994 |

(List continued on next page.)

OTHER PUBLICATIONS

Assoc. of the Nonwoven Fabrics Industry, "The Needlepunch Primer", INDA pp. 1–29 (1995).
Foster, "Needlepunching A Unique Sector," FW: Nonwovens Manufacturing, pp. 2–6 (1996).

Primary Examiner—Cheryl A. Juska
(74) Attorney, Agent, or Firm—Fish & Richardson, P.C.

(57) ABSTRACT

Lightweight, non-woven loop products for hook-and-loop fastening are disclosed, as are methods for making them and end products employing them. The products are non-woven webs of entangled fibers of substantial tenacity, the fibers forming both a sheet-form web body and hook-engageable, free-standing loops extending from the web body. The product is stretched and stabilized to produce spaced-apart loop clusters extending from a very thin web of taut fibers. In important cases a binder is added to stabilize the product in its stretched condition. An example of the loop product is produced by needle-punching a batt of staple fibers in multiple needle-punching operations, applying a foamed acrylic binder, and then stretching the needled batt and curing the binder with the batt stretched. Other forming techniques are disclosed and several novel articles and uses employing such loop products are described, such as for filters and fasteners.

49 Claims, 13 Drawing Sheets

U.S. PATENT DOCUMENTS

| | | |
|---|---|---|
| 4,154,889 A | 5/1979 | Platt |
| 4,223,059 A | 9/1980 | Schwarz |
| 4,258,097 A | 3/1981 | Benedyk ............... 428/224 |
| 4,295,251 A | 10/1981 | Tatham et al. |
| 4,320,167 A | 3/1982 | Wishman ............... 428/89 |
| 4,363,845 A | 12/1982 | Hartmann |
| 4,377,889 A | 3/1983 | Tatham et al. |
| 4,379,189 A | 4/1983 | Platt |
| 4,389,442 A | 6/1983 | Pickens, Jr. et al. |
| 4,391,866 A | 7/1983 | Pickens, Jr. et al. |
| 4,418,104 A | 11/1983 | Kiyomura et al. |
| 4,424,250 A | 1/1984 | Adams et al. ............ 428/198 |
| 4,446,189 A | 5/1984 | Romanek |
| 4,451,314 A | 5/1984 | Knoke et al. |
| 4,451,315 A | 5/1984 | Miyazaki |
| 3,152,381 A | 10/1984 | Priester, Jr. et al. |
| 4,490,425 A | 12/1984 | Knoke et al. |
| 4,536,439 A | 8/1985 | Forsten |
| 4,600,605 A | 7/1986 | Nakai et al. |
| 4,600,618 A | 7/1986 | Raychok, Jr. et al. ........ 428/92 |
| 4,624,116 A | 11/1986 | Rogers ............... 66/193 |
| 4,645,699 A | 2/1987 | Neveu ............... 428/95 |
| 4,654,246 A | 3/1987 | Provost et al. ............ 428/88 |
| 4,739,635 A | 4/1988 | Conley et al. ............ 66/190 |
| 4,750,443 A | 6/1988 | Blaustein et al. |
| 4,761,318 A | 8/1988 | Ott et al. ............... 428/85 |
| 4,806,300 A | 2/1989 | Walton et al. |
| 4,931,343 A | 6/1990 | Becker et al. ............ 428/95 |
| 4,973,326 A | 11/1990 | Wood et al. |
| 4,981,749 A | 1/1991 | Kubo et al. ............ 428/129 |
| 4,992,124 A | 2/1991 | Kurihara et al. |
| 5,032,122 A | 7/1991 | Noel et al. ............ 604/391 |
| 5,066,289 A | 11/1991 | Polski |
| 5,144,730 A | 9/1992 | Dilo |
| 5,151,320 A | 9/1992 | Homonoff et al. |
| 5,214,942 A | 6/1993 | Peake, III et al. ............ 66/194 |
| 5,216,790 A | 6/1993 | Eschenbach |
| 5,256,231 A | 10/1993 | Gorman et al. |
| 5,267,453 A | 12/1993 | Peake, III et al. ............ 66/194 |
| 5,304,162 A | 4/1994 | Kuen ............... 604/391 |
| 5,326,612 A | 7/1994 | Goulait |
| 5,380,313 A | 1/1995 | Goulait et al. ............ 604/391 |
| 5,382,461 A | 1/1995 | Wu ............... 428/86 |
| 5,383,872 A | 1/1995 | Roessler et al. ............ 604/391 |
| 5,386,595 A | 2/1995 | Kuen et al. ............ 2/400 |
| 5,391,424 A | 2/1995 | Kolzer ............... 428/220 |
| 5,403,302 A | 4/1995 | Roessler et al. |
| 5,407,439 A | 4/1995 | Goulait ............... 604/391 |
| 5,407,722 A | 4/1995 | Peake, III et al. ............ 428/88 |
| 5,423,789 A | 6/1995 | Kuen |
| 5,447,590 A | 9/1995 | Gilpatrick ............ 156/178 |
| 5,449,530 A | 9/1995 | Peake, III et al. ......... 427/244 |
| 5,470,417 A | 11/1995 | Goulait ............... 156/201 |
| 5,476,702 A | 12/1995 | Datta et al. |
| 5,500,268 A | 3/1996 | Billarant ............... 428/100 |
| 5,518,795 A * | 5/1996 | Kennedy et al. ............ 428/100 |
| 5,531,732 A | 7/1996 | Wood |
| 5,542,942 A | 8/1996 | Kline et al. |
| 5,565,255 A | 10/1996 | Young et al. |
| 5,569,233 A | 10/1996 | Goulait |
| 5,586,371 A | 12/1996 | Thomas |
| 5,595,567 A | 1/1997 | King et al. |
| 5,605,729 A | 2/1997 | Mody et al. ............... 428/37 |
| 5,611,791 A | 3/1997 | Gorman et al. |
| 5,614,232 A | 3/1997 | Torigoe et al. |
| 5,614,281 A | 3/1997 | Jackson et al. |
| 5,615,460 A | 4/1997 | Weirich et al. |
| 5,616,155 A | 4/1997 | Kronzer ............... 51/295 |
| 5,616,394 A | 4/1997 | Gorman et al. |
| 5,618,583 A | 4/1997 | Young et al. |
| 5,620,779 A | 4/1997 | Levy et al. |
| 5,622,578 A | 4/1997 | Thomas |
| 5,624,427 A | 4/1997 | Bergman et al. |
| 5,647,864 A | 7/1997 | Allen et al. |
| 5,654,070 A | 8/1997 | Billarant ............... 428/100 |
| 5,664,302 A | 9/1997 | Thomas |
| 5,669,900 A | 9/1997 | Bullwinkel et al. ......... 604/391 |
| 5,685,756 A | 11/1997 | Noda |
| 5,695,377 A | 12/1997 | Triebes et al. |
| 5,699,593 A | 12/1997 | Jackson |
| 5,707,707 A | 1/1998 | Burnes et al. ............ 428/95 |
| 5,722,968 A | 3/1998 | Datta et al. ............ 604/391 |
| 5,736,214 A | 4/1998 | Billarant |
| 5,747,584 A | 5/1998 | Noda |
| 5,773,120 A | 6/1998 | Deka et al. |
| 5,843,057 A | 12/1998 | McCormack |
| 5,858,515 A | 1/1999 | Stokes et al. |
| 5,888,607 A | 3/1999 | Seth et al. |
| 5,891,547 A * | 4/1999 | Lawless ............... 428/92 |

FOREIGN PATENT DOCUMENTS

| | | |
|---|---|---|
| EP | 0 605 013 A1 | 7/1994 |
| EP | 0 765 616 A1 | 2/1997 |
| EP | 0 780 505 A2 | 6/1997 |
| EP | 0 937 420 A2 | 8/1999 |
| GB | 2 285 093 A | 6/1995 |
| GB | 2 290 052 | 12/1995 |
| JP | 2-41156 | 2/1990 |
| JP | 2-191735 | 7/1990 |
| JP | 4-56008 | 5/1992 |
| JP | 6-33359 | 2/1994 |
| JP | 6-123061 | 5/1994 |
| JP | 6-141913 | 5/1994 |
| JP | 07300752 A | 11/1994 |
| JP | 7-231842 | 5/1995 |
| JP | 71-71011 | 11/1995 |
| JP | 8-27657 | 1/1996 |
| JP | 9-195153 | 7/1997 |
| JP | 9-195154 | 7/1997 |
| JP | 9-309168 | 12/1997 |
| JP | 10-146207 | 6/1998 |
| JP | 10-151005 | 6/1998 |
| JP | 10-165207 | 6/1998 |
| WO | WO 92/01401 | 2/1992 |
| WO | WO 95/17111 | 6/1995 |
| WO | WO 96/03101 | 2/1996 |
| WO | WO 96/14459 | 5/1996 |
| WO | WO 98/33410 | 8/1998 |

* cited by examiner

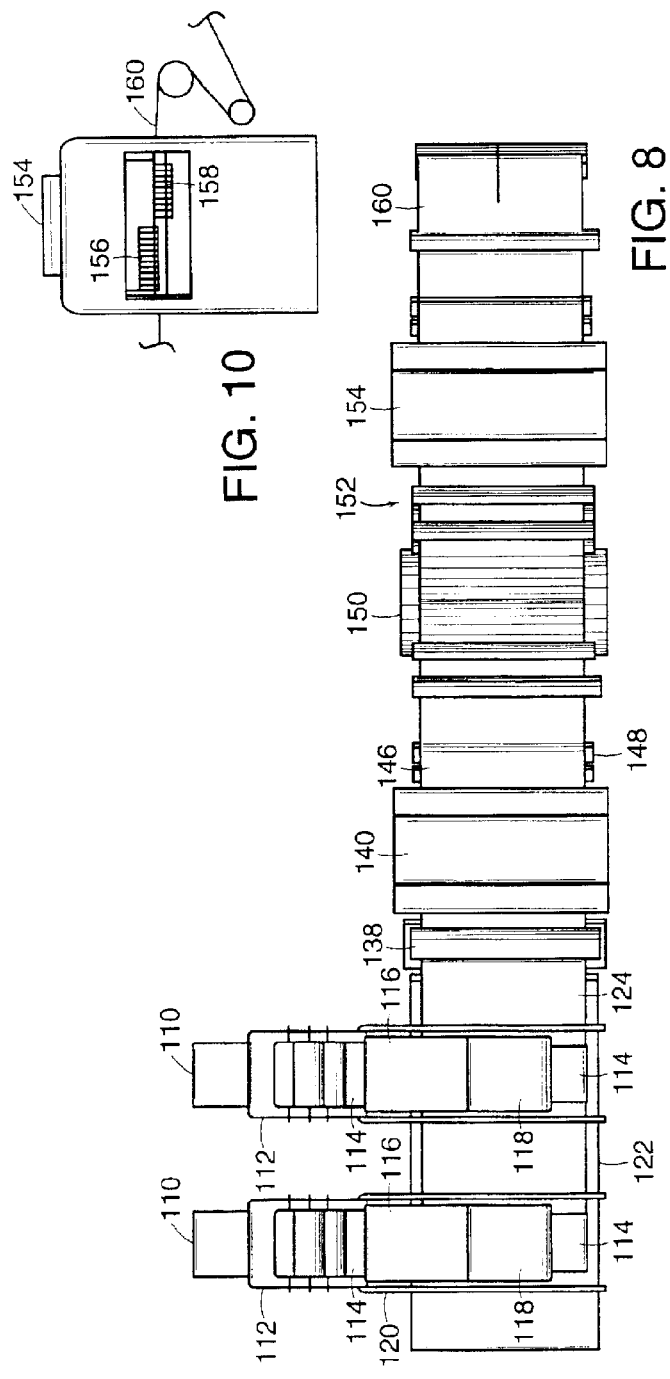
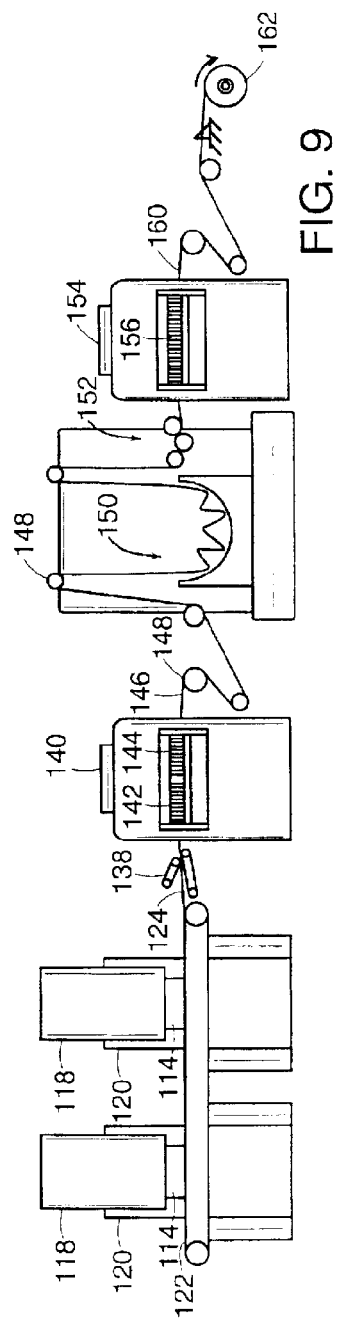
FIG. 8
FIG. 9
FIG. 10

LOOP MATERIAL FOR TOUCH FASTENING

CROSS-REFERENCE TO RELATED APPLICATIONS

This application is a continuation of U.S. Ser. No. 09/262,159, filed Mar. 3, 1999, now U.S. Pat. No. 6,329,016, which was a continuation-in-part of PCT/US98/18401 filed Sep. 3, 1998, which published in English on Mar. 11, 1999, which was a continuation-in-part of U.S. Ser. No. 08/922,292, filed Sep. 3, 1997.

BACKGROUND OF THE INVENTION

This invention relates to loop material, particularly to material to be engaged with hooking members to form a fastening, to its manufacture and use, and to fasteners comprising such loop material.

In the production of woven and non-woven materials, it is common to form the material as a continuous web that is subsequently spooled. In woven and knit loop materials, loop-forming filaments or yarns are included in the structure of a fabric to form upstanding loops for engaging hooks. As hook-and-loop fasteners find broader ranges of application, especially in inexpensive, disposable products, some forms of non-woven materials have been suggested to serve as a loop material to reduce the cost and weight of the loop product while providing adequate closure performance in terms of peel and shear strength. Nevertheless, cost of the loop component has remained a major factor limiting the extent of use of hook and loop fasteners.

To adequately perform as a loop component for touch fastening, the loops of the material must be exposed for engagement with mating hooks. Unfortunately, compression of loop material during packaging and spooling tends to flatten standing loops. In the case of diapers, for instance, it is desirable that the loops of the loop material provided for diaper closure not remain flattened after the diaper is unfolded and ready for use.

SUMMARY OF THE INVENTION

We have realized that non-woven fabrics constructed with certain structural features are capable of functioning well for their intended purpose as hook-engageable loop fabrics, while providing particular advantage in regard to expense of manufacture and other properties.

According to one aspect of the invention, a loop component of a hook and loop fastener is provided. The loop component has a nonwoven body of fibers with a basis weight of less than about 4 ounces per square yard (preferably, less than about 2 ounces per square yard). The fibers form a sheet-form base containing taut sections of fiber extending within a common plane between tightened knots of fibers, and a great multiplicity of loop formations dispersed across the base. Each loop formation has a trunk of fibers drawn together by taut fibers of the base and extending from an associated knot in the common plane of the base, and multiple hook-engageable loops formed of fibers of the trunk and extending from the trunk for engagement by hooks of a mating component.

In some embodiments, the majority of fibers forming the trunks and hook-engageable loops are crimped.

In some embodiments, the knots of the base each correspond to an associated previous penetration of the body of fibers by a needle. The body of fibers, in some such cases, may include crimped staple fibers.

In some loop components, the fibers comprising the trunks of the loop formations are secured together by a cured binder in interstices within the trunks. Preferably, the cured binder composes between about 20 and 40 percent of the total weight of the body of fibers.

In some cases, the fibers comprising the trunks of the loop formations are secured together by fused surface portions of at least some of the fibers comprising the trunks.

In some cases, the fibers comprising the trunks of the loop formations are secured together by interlocking crimps of the fibers.

In some embodiments, at least some of the fibers comprising the trunks of the loop formations each have a thickness that undulates along their length.

For some applications, the loop component also includes a resilient layer of foam laminated to the base of the body of fibers.

A layer of resin is, for some applications, laminated to the base of the body of fibers. The resin layer may form hook projections shaped to engage the loops of the component, for instance.

Preferably, the hook-engageable loops extend to an average loop height, measured as the perpendicular distance from the sheet-form base, of between about 0.020 and 0.060 inch, and the average loop height is between about 0.5 and 0.8 times the overall thickness of the body of fibers (defined to include the sheet-form base and a majority of the loops).

The sheet-form base has, in presently preferred embodiments, between about 50 and 1000 tightened knots per square inch of area, from which hook-engageable loop formations extend.

In some preferred configurations, the body of fibers is generally composed of fibers having a tenacity of at least 2.8 grams per denier.

For some important applications, the loop component preferably has a Gurley stiffness of less than about 300 milligrams.

By "hook-engageable" and similar terms used above and throughout this specification, we mean that the loop material defines openings of size adequate to receive the tip or head portion of a male fastener element (such as a hook-shape or mushroom-shape element, for instance) for forming a fastening, and that the openings are exposed and extended for engagement.

By the word "entanglements" we mean that the nodes at which a multiplicity of fibers are intertwined in the non-woven web. These entanglements may be relatively loose, as formed directly by a needling process, for instance, or tightened after formation of the entanglements. By the word "knots" we mean entanglements that have been tightened by applying tension to their intertwined fibers in at least one direction in the plane of the web, and remain in an at least partially tightened state.

By "stabilized", we mean that the web is processed to generally maintain its planar dimensions. In other words, a web "stabilized" in a stretched condition will generally maintain its stretched dimensions and not significantly relax or stretch further under conditions of normal use. One way of "stabilizing" the web, for instance, is by solidifying binder at a significant proportion of its entanglements.

We have also realized that such loop fabrics as just described are advantageously produced by employing certain manufacturing techniques and methods.

According to another aspect of the invention, a method of forming a loop fastener component is provided. The method includes the steps of:

(1) providing a sheet-form mat of fibers;

(2) tensioning the base fiber by applying tension across the width of the mat, thereby forming a tensioned web; and (3) stabilizing the web in its tensioned state.

The mat includes at least one base fiber of a length greater than the width of the mat and extending substantially across the mat, and loop fibers freely disposed within the mat. The tensioned web is formed by discrete, taut portions of base fiber extending between tightened entanglements. Relative movement between portions of the base fiber during tensioning draws together portions of the loop fibers to form upstanding, hook-engageable loops extending from the entanglements within the tensioned web. The stabilized web and loops have a combined weight of less than about 4 ounces per square yard. in some cases, the step of stabilizing includes solidifying a binder within the entanglements of the tensioned web.

Preferably, the step of tensioning increases the width of the mat by at least 20 percent.

In some embodiments, the step of providing a sheet-form mat of fibers includes continuously spinning the base fiber onto a supporting surface in a predetermined, overlapping pattern. In some cases, a pulsating air jet is impinged against the base fiber under conditions which cause the fiber to assumed a crimped form as it is spun.

In some embodiments, the base fiber has a cross-sectional property, such as thickness or cross-sectional area, that varies along its length.

According to another aspect of the invention, a method of forming a loop fastener component for hook-and-loop fastening includes stretching a generally planar non-woven batt of entangled fibers by at least 20 percent (preferably, at least 50 percent) in at least one direction in its plane, thereby producing a stretched web of weight less than about 4 ounces per square yard and having a generally planar web body with hook-engageable loops extending therefrom. A substantial number of fibers of the body are regionally taut in the plane of the web body as a result of the stretching, and extend in different directions radiating from bases of the loops. Afterwards, the web is stabilized in its stretched condition.

Preferably, the batt is retained against shrinking in a perpendicular direction within its plane during stretching.

In some embodiments, after stretching the batt in one direction the batt is stretched by at least 20% in another, perpendicular direction. In some other cases, the batt is simultaneously stretched by at least 20% in two perpendicular directions within the plane of the batt.

The stretching preferably causes the regionally taut fibers of the web body to be trained about loop-forming fibers in the bases of the loops, the batt being stretched in a manner that the loop-forming fibers form free-standing formations that extend from the plane of the web body, each formation containing multiple fibers and forming multiple, hook-engageable loops.

According to another aspect of the invention, a method of forming a loop fastener component for hook-and-loop fastening includes the steps of:

(1) providing a generally planar length of non-woven batt of entangled fibers, the batt having a thickness that varies across its width from one longitudinal edge thereof to an opposite longitudinal edge thereof;

(2) stretching the batt widthwise, thereby increasing the width of the batt by at least about 20 percent and producing a stretched web having a generally planar web body with hook-engageable loops extending therefrom (a substantial number of fibers of the body being regionally taut in the plane of the web body, and extending in different directions radiating from bases of the loops); and then (3) stabilizing the web in its stretched condition. Advantageously, the stretching causes the thickness of the batt to become substantially uniform over its width.

Preferably, the stretched batt has weight less than about 4 ounces per square yard.

In some preferred embodiments, the stretched batt has width at least about twice the width of the batt prior to stretching.

The invention can provide a very inexpensive loop product which can very effectively engage and retain hooks, such as in hook-and-loop fasteners. The loop product can be particularly useful in combination with extremely small, inexpensive molded hooks as fasteners for disposable products, such as diapers, medical devices or packaging. We have found, for instance, that the structure of the extended "loop trees" of the material, described below in more detail, helps to prevent permanent flattening of the loops and provides some advantageous crush resistance.

BRIEF DESCRIPTION OF THE DRAWINGS

FIG. 8 is a top view of an apparatus for making a nonwoven fabric.

FIG. 9 is a side elevational view of the apparatus of FIG. 8.

FIG. 10 shows an alternative arrangement of the second needling stage of the apparatus of FIG. 9.

DESCRIPTION OF EMBODIMENTS

Figure 1:
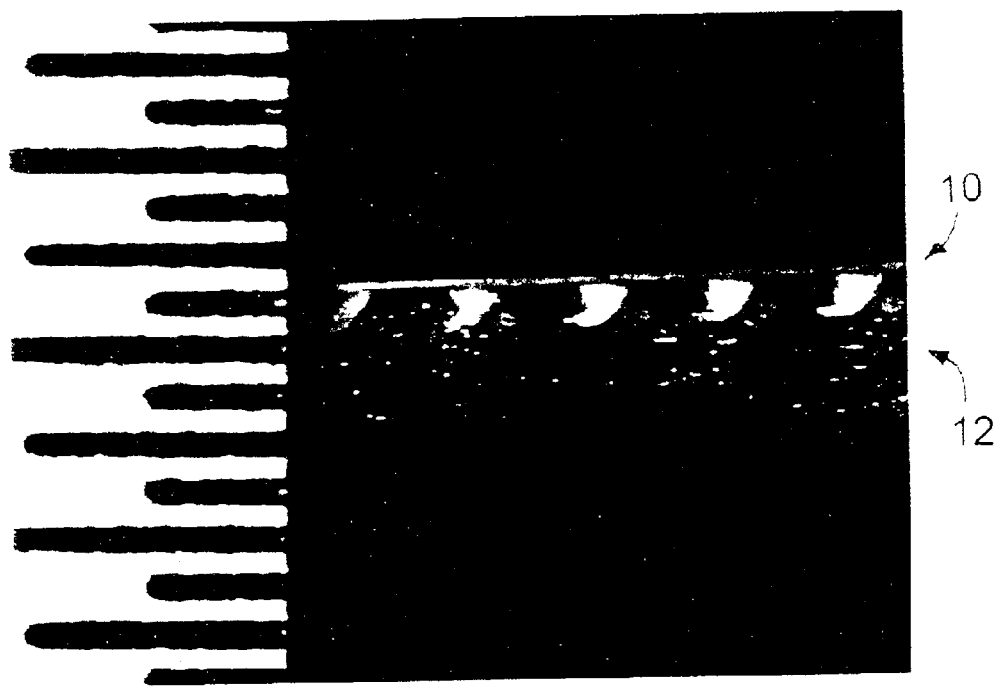
FIG. 1 is an enlarged side view of a hook-and-loop fastener.
Figure 2:
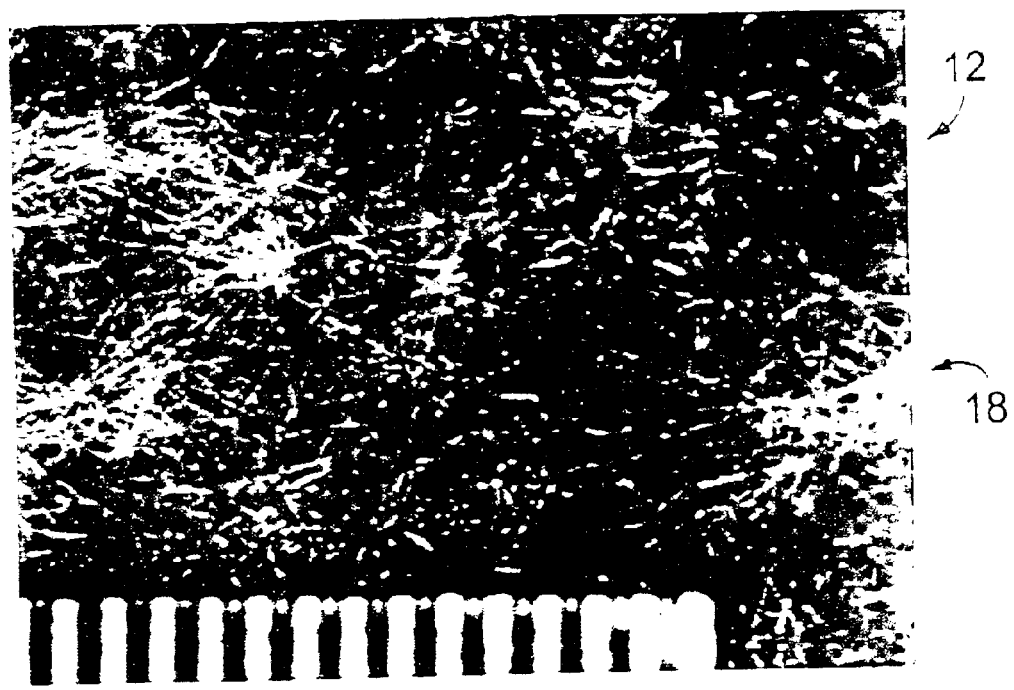
FIG. 2 is an enlarged plan view of a loop fastener product.
Figure 2A:
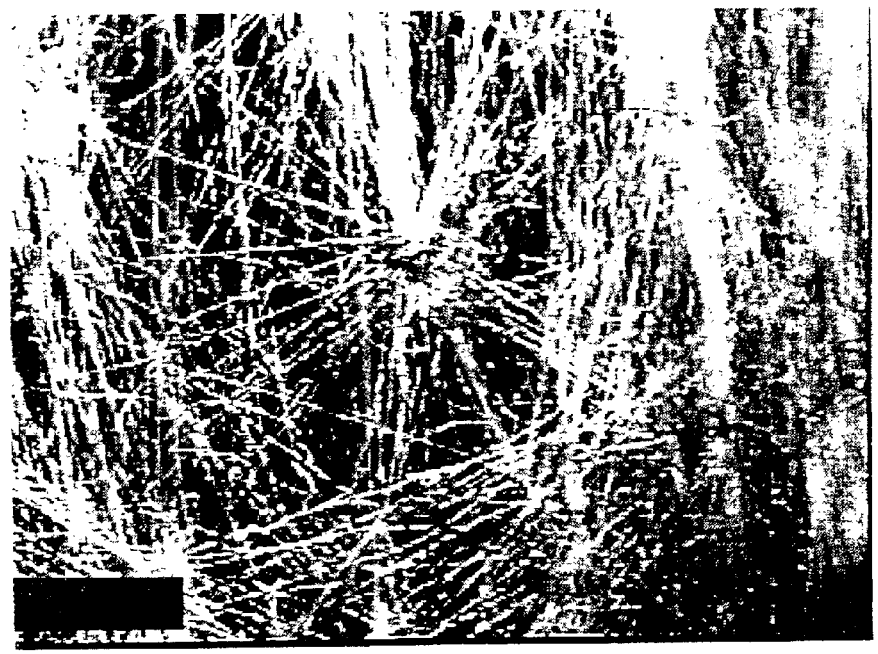
FIG. 2A is a plan view of a loop fastener product, enlarged 50× and showing the structure of the web.

Referring first to FIG. 1, a molded hook fastener product 10 is shown engaging the loops of a very thin loop product 12. The photograph is quite enlarged, as shown by the scale on the left side of the photograph. The minor divisions of the scale each represent a length of 1/64th (0.0156) inch (0.40 mm). Hook product 10 is of the CFM-29 designation, available from Velcro U.S.A Inc. of Manchester, N.H., U.S.A., and has hooks of only 0.015 inch (0.38 mm) height. Referring also to FIGS. 2 and 2A, loop product 12, a feature of the present invention, is very thin (as evidenced by the scale of the photographs and its lack of opacity) and has relatively free fibers forming loops extending from one side of a continuous, tangled mat of fibers. In this and the following photographs all scale graduations, unless otherwise marked, are in 0.0156 (1/64) inch (0.40 mm) increments.

As shown in FIG. 2, and especially in FIG. 2A, a substantial number of the fibers of the mat of loop product 12 are taut (i.e., not slack, regionally straight), extending between knots 18 of the loop product fabric. The taut fibers have been pulled taught by stretching the mat of tangled fibers in at least one direction in the plane of the fabric mat. Preferably, the mat is held against shrinking in one direction as it is stretched in a second, perpendicular direction. More preferably, the mat is simultaneously stretched in two perpendicular directions. The individual fibers of the mat follow no definite pattern as in a woven product, but extend in various directions within the plane of the fabric mat. The loops that extend from the loop product are of the same fibers that comprise the mat but extend beyond the general mass of the mat, out of the plane of the mat, generally from associated knots 18. The knot density of the sample shown in the photograph was determined to be approximately 180 knots per square inch by counting the number of visible knots within a given square area. The knots themselves are fairly tight, made up of several monofilament fibers, and are interconnected by the taut fibers seen running between them. In between knots, the thin fiber mat is not very dense and is sheer enough to permit images to be readily seen through it. For low cost application, the fabric preferably weighs less than about 2 ounces per square yard (68 grams per square meter).

In this particular embodiment, the fibers of the mat are held in their taut, straightened condition by a water-based, acrylic binder (not visible in the photograph) applied to the side of the mat opposite the loops to bind the mat fibers in their taut condition to stabilize the areal dimensions of the fabric, and to secure the loops at their associated knots. The binder generally ranges between 20 and 40% of the total weight of the fabric and in the presently preferred embodiments accounts for about one third of the total product weight. The resulting fabric is dimensionally stable and strong enough to be suitable for further processing by standard fabric-handling techniques. The fabric also has a slight stiffness, like a starched felt, which can be mitigated by softeners or mechanical working if desired.

Figure 2B:
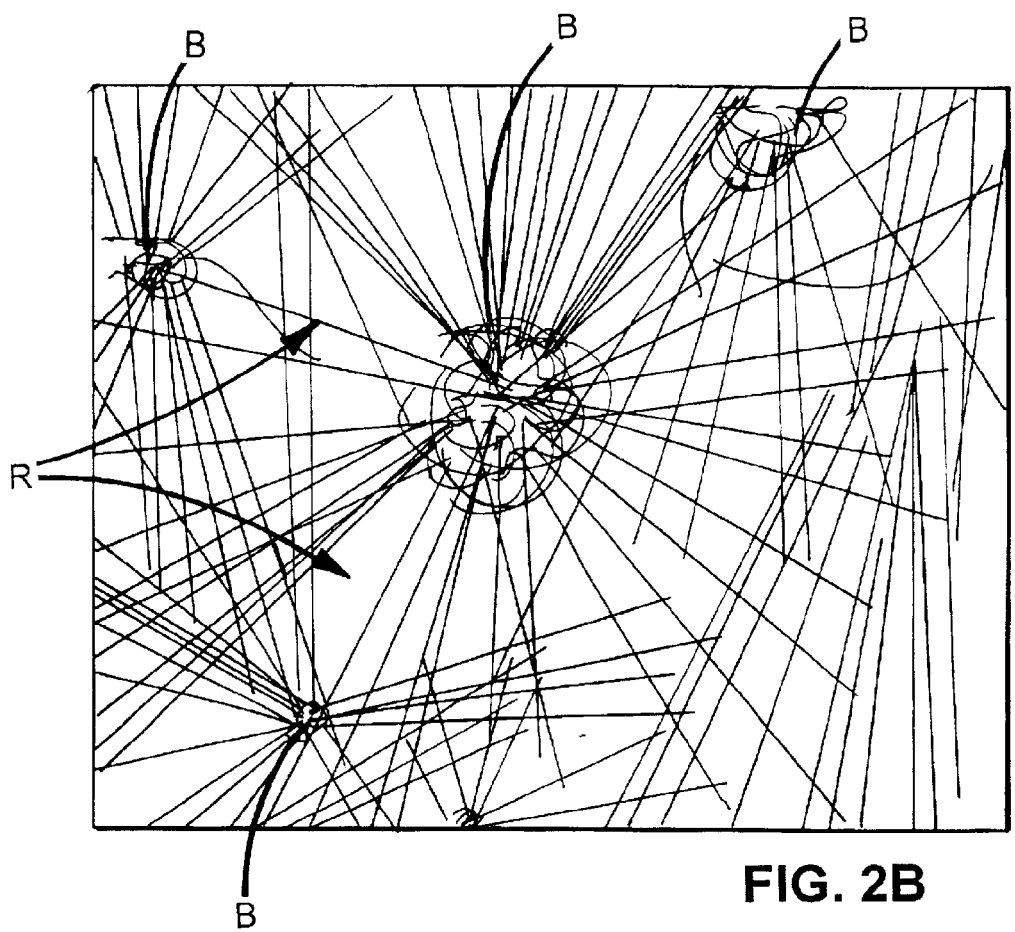
FIG. 2B is a schematic view of the structure shown in FIG. 2A.

The schematic view of FIG. 2B illustrates the structure of planar web 12, as viewed from one face of the web. In this view, the loop-engageable loops extend out of the plane of the web, from one side. Web 12 is composed of a non-uniform distribution of entangled fibers, with relatively high concentrations of the fibers at the bases, B, of corresponding loop structures, and relatively lower concentrations of the fibers in regions, R, lying between loop bases, B. The relatively high concentrations of fibers at bases B correspond to tightened fiber entanglements. As illustrated in this sketch, and visible in FIG. 2A, a substantial number of the fibers in the regions, R, between loop bases are taut in the plane of the web, extending in different directions radiating from loop bases, B. By "taut", we mean that a large percentage of these inter-base fibers have no give or slack, such that they may transmit an applied tensile force with little or no displacement. We believe that the taut fiber portions extending across the sparse regions between loop bases account for some of the beneficial properties of the loop product, giving it a perceptibly high strength-to-weight ratio as a fastener component.

Near the center of both FIG. 2A and FIG. 2B is a particularly visible loop base B, from which taut fibers can be seen emanating in a radial pattern. Also note that there are some fibers which are wrapped at least partially about other fibers of the loop base. These wrapping fibers are so wrapped as the result of stretching, during which straightening fibers encounter loop fibers extending through the planar web. As the web is further stretched, the loop fibers provide obstructions about which the straightening web base fibers are trained as they are displaced within the web plane. Thus the bases, B, of the loop structures contain both portions of the loop-forming fibers extending both in and out of the plane of the web, and trained portions of taut fibers lying generally only in the plane of the web. The trained portions of the taut fibers within the loop bases therefore contribute, as the web is stretched, to the definition of the free-standing loop formations. When the web is stabilized by binder, for instance, these bases B become relatively rigid nodes and, importantly, provide anchoring for their associated loop structures. Thus the stretched and stabilized web, in some respects, resembles a planar truss, with its taut radiating fibers forming tensile members between base nodes. As the taut fibers may be readily "bent" out of their plane as the web flexes, the structure retains an advantageously high flexibility while resisting elongation and shrinkage within its original plane.

The individual fibers of loop fabric 12 shown in FIG. 2 have low denier and substantial tenacity (i.e., tensile strength per unit diameter) to work with very small hooks such as those illustrated in FIG. 1. Fibers with tenacity values of at least 2.8 grams per denier have been found to provide good closure performance, and fibers with a tenacity of at least 5 or more grams per denier (preferably even 8 or more grams per denier) are even more preferred in many instances. In general terms for a loop-limited closure, the higher the loop tenacity, the stronger the closure. The fibers of fabric 12 of FIGS. 1 and 2 are 6 denier staple polyester fibers (cut to four inch lengths) and as a result of the method of the manufacture, are in a drawn, molecular oriented state, having been drawn with a draw ratio of at least 2:1 (i.e., to at least twice their original length) under cooling conditions that enable molecular orientation to occur, to provide a fiber tenacity of about 3.6 grams per denier. The fibers in this example are of round cross-section and are crimped at about 7.5 crimps per inch (3 crimps per cm). Such fibers are available from E.I. Du Pont de Nemours & Co., Inc., in Wilmington, Del. under the designation T-3367 PE T-794W 6×4. The loop fiber denier should be chosen with the hook size in mind, with lower denier fibers typically selected for use with smaller hooks. For low-cycle applications for use with larger hooks (and therefore preferably larger diameter loop fibers), fibers of lower tenacity may be employed.

As an alternative to round cross-section fibers, fibers of other cross-sections having angular surface aspects, e.g. fibers of pentagon or pentalobal cross-section, can enhance knot tightening for certain applications. Regardless of the particular construction of the individual fibers, they, are selected to have a surface character that permits slippage within the knot-forming entanglements during tightening so as to enable stretching the batt without undue fiber breakage.

Figure 3A:
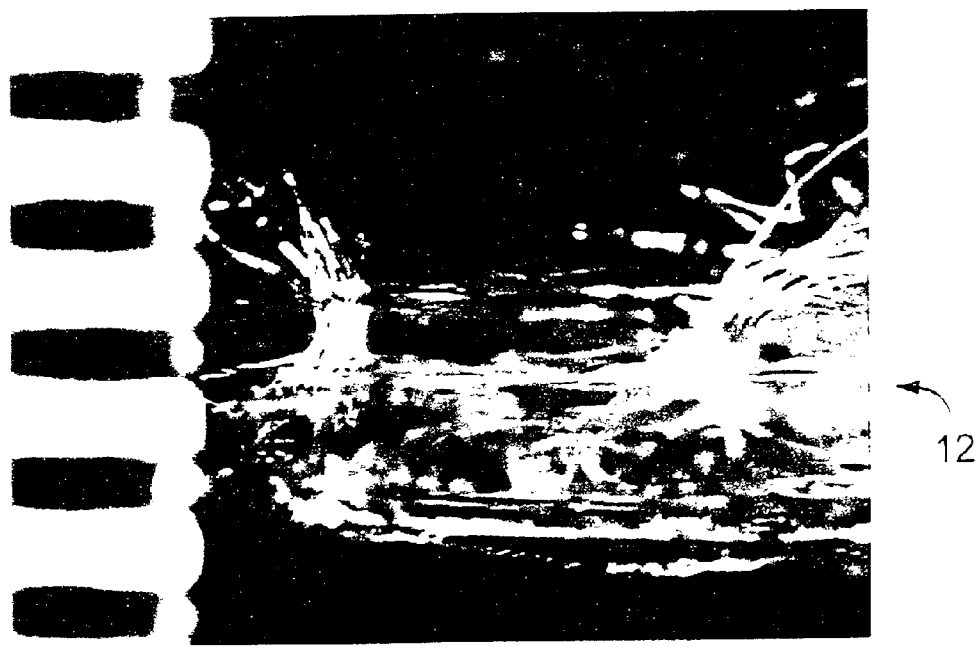
FIG. 3A is a highly enlarged side view of the loop fastener product of FIG. 2.
Figure 3B:
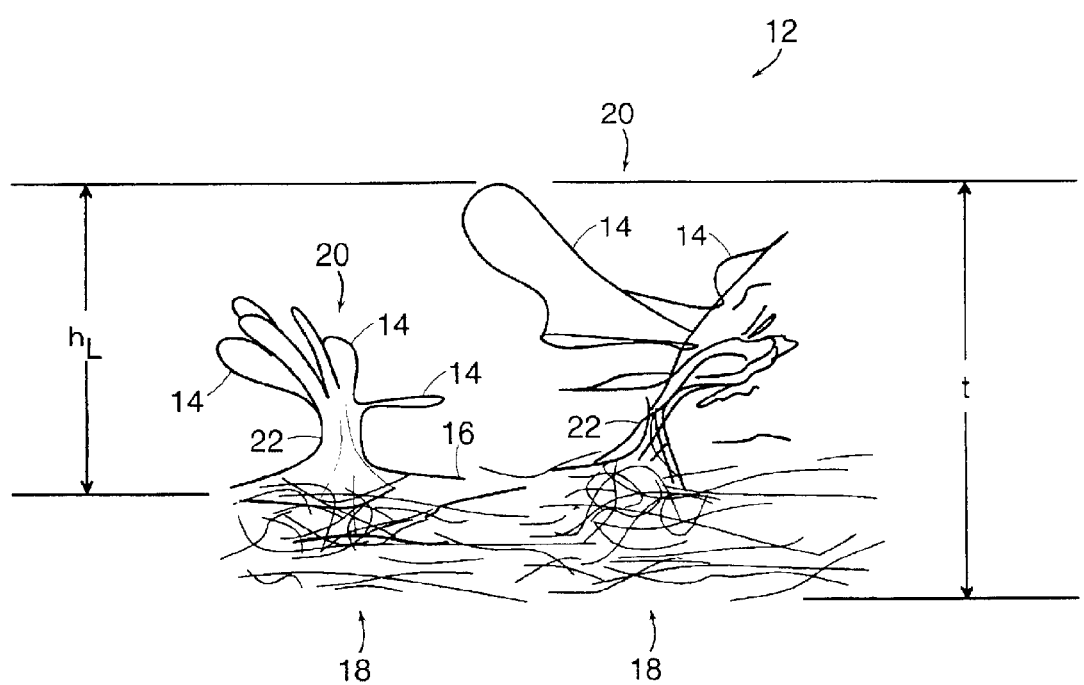
FIG. 3B is a sketch of the structure in the foreground of FIG. 3A.

Referring to FIGS. 3A and 3B, the loops 14 of loop fabric 12 project primarily from one side of the fabric. The stabilizing binder, in this case, is applied to the other side. The loop product is extremely thin for use with very small hooks. The product shown, for instance, works well with hooks of about 0.015 inch (0.4 mm) height and has a loop height $h_L$ (i.e., the height of loops 14 from the near general surface of fiber mat 16) of about 0.055 inch (1.40 mm). The loop product has an overall thickness, t, including a majority of the loops, of only about 0.090 inch (2.3 mm). When measuring loop height in products without a visibly distinguishable upper mat surface, we define the near surface of the mat to be the lowest planar surface above about 80 percent of the total mass of fibers. The loops of the loop structures preferably vary in height for good engagement, and the average loop height (i.e., the distance from the top of the loop to the near surface of the mat) should generally be at least about the height of the hooks with which the loop product is to be used, and preferably between 2 and 10 times the head height of the hooks used for applications requiring good shear strength. Importantly, individual loops of the loop structures should be large enough to accept the head of an individual hook. For fasteners which are primarily loaded in peel, or by loads perpendicular to the plane of the base, the loops may be up to 15 times the head height of the hooks. For example, for use with 0.015 inch (0.4 mm) CFM-29 hooks (which have a head height of 0.006 inch or 0.15 mm), the average height $h_L$ of the loops should be between about 0.012 and 0.060 inch (0.3 and 1.5 mm) for good shear performance. For use with 0.097 inch (2.5 mm) CFM-24 hooks (which have a head height of 0.017 inch or 0.43 mm and are also available from Velcro U.S.A. Inc.), the average height of the loops should be at least 0.035 inch (0.89 mm) and may be as high as 0.250 inch (6.4 mm) for applications focusing on peel loading. For low cost, flexible loop fabrics, the average loop height should generally be between about 0.020 and 0.060 inch (0.5 and 1.5 mm), and should be between about 0.5 and 0.8 times the overall thickness, t, of the loop product.

Figure 3C:
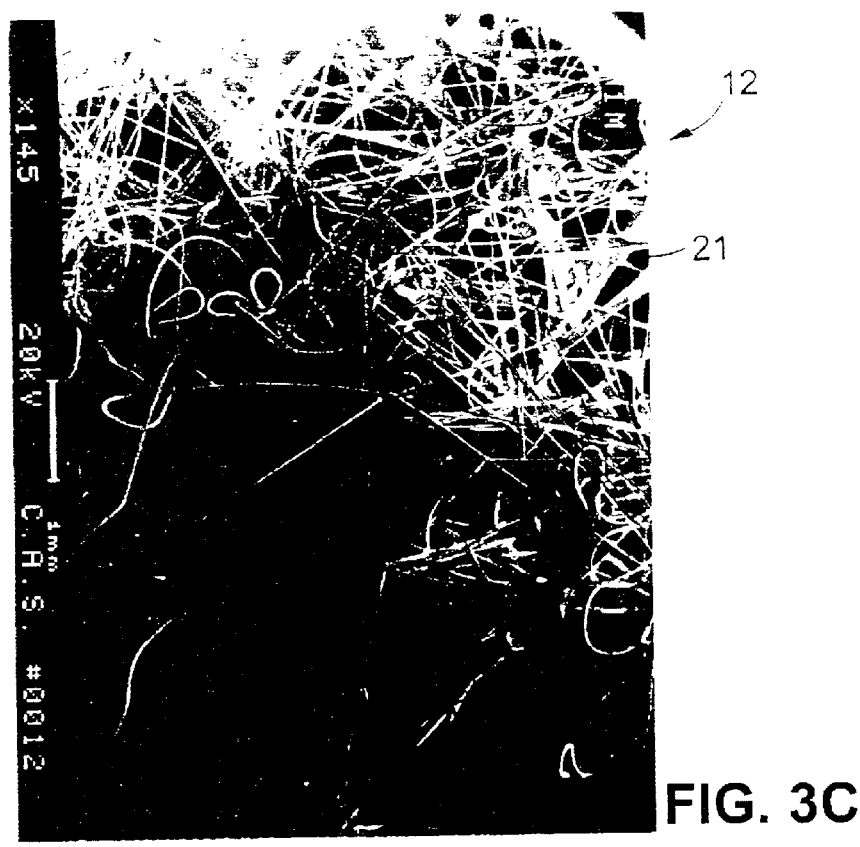
FIG. 3C is a highly enlarged plan view of a portion of the loop fastener product of FIG. 2.

As seen in FIGS. 3A and 3B, loops 14 extend from free-standing clusters of loop fibers extending from the fibrous mat 16. The clusters 20 which have several monofilament loops 14 extending from a common elongated, substantially vertical trunk 22 we call "loop trees". Another example of a "loop tree" is seen in FIG. 3C. Each loop tree 20 extends from a corresponding knot 18 in which the loops of the cluster are anchored. Interstices between individual filaments in the trunk portion 22 and base of each tree, and in each knot 18, provide paths for the wicking of liquid binder, under the influence of surface tension of the liquid binder, to provide additional localized stiffness and strength. The vertical stiffness of the trunk portion 22 of each tree, provided both by the bundling of multiple trunk fibers by circumscribing fibers of the base and by the cured binder, helps the trees to "stand proud", or erect, to present their associated loops for engagement. This vertical stiffness acts to resist permanent crushing or flattening of the loop structures, which can occur when the loop material is spooled or when the finished product to which the loop material is later joined is compressed to be fit into packaging. Resiliency of the trunk portion 22, especially at its juncture with the base, enables trees that have been "toppled" by heavy crush loads to right themselves when the load is removed. The trunk portions 22 should not be too stiff at their interface with the base of the loop material, otherwise the material would lose its soft hand and be less useful for garment applications.

Importantly, the density of clusters in the plan view is very low (FIGS. 2 and 2A), leaving sufficient room between the "branches" of neighboring trees to accommodate hooks and deflected loop material during engagement. By leaving adequate room between neighboring loop trees, the heads of many of the hooks of a mating material extend down to the base of the loop material during engagement, without flattening the loop structures. This high penetration rate helps to provide a high engagement rate as the penetrating hooks grab loops as a result of very small relative shear motion between the hooks and the loops while the loop forest is thus penetrated.

Accumulations of solidified binder 21 can be seen in the knots in the highly magnified plan view of FIG. 3C. Applied in liquid form in this example, preferably before the knots are tightened, the binder contributes to securing the loops against being pulled out of the web.

Referring back to FIG. 1, with proper clearance between loops for the accommodation of hooks, the fully engaged fastener (i.e., the loop product and mating hook product together) has an overall thickness of only the sum of the thickness of the hook product (including hooks) and the "ground" portion of the loop product (i.e., the thickness of the mat 16 between loop clusters, FIG. 3B). In other words, the free standing loops of the loop product do not add to the thickness of the completed fastener. Because of the ultra-thin ground portion 16 of the loop product disclosed herein (see FIG. 3B), the combination of loop product 12 with mating hook product 10 provides a fastening of very small thickness. For example, the engaged fastener of FIG. 1 has an overall thickness of only about 0.050 inch (1.3 mm; thinner, in this case, than the overall thickness of the unengaged loop product, as the taller loop clusters are somewhat compressed by the hook product engaged with shorter loop clusters).

In addition to being advantageously thin, loop fabric formed according to the new principles is particularly flexible. Flexibility can be very important in some fastener applications, especially when the fastener must flex during use, as when used on an article of apparel. In such instances, the loop product of the invention should have a bending stiffness of less than about 300 milligrams, preferably less than about 100 milligrams, as measured with a Gurley stiffness tester. More details on the use of Gurley stiffness testers can be found in Method T 543 OM-94, published in 1984 by the Technical Association of Pulp and Paper (TAPPI).

Various synthetic or natural fibers may be employed in the invention. In some applications, wool and cotton may provide sufficient fiber strength. Presently, thermoplastic staple fibers which have substantial tenacity are preferred for making thin, low-cost loop product that has good closure performance when paired with very small molded hooks. For example, polyolefins (e.g., polypropylene or polyethylene), polyesters (e.g., polyethylene terephthalate), polyamides (e.g., nylon), acrylics and mixtures, alloys, copolymers and coextrusions thereof are suitable. Polyester is presently preferred.

For a product having some electrical conductivity, a small percentage of metal fibers may be added. For instance, loop products of up to about 5 to 10 percent fine metal fiber, for example, may be advantageously employed for grounding or other electrical applications.

Various binders may be employed to stabilize the fabric. By "binder" we mean a material within the mat (other than the fibers forming the main fastener loops) that secures the loop fibers at associated knots. In some applications, the binder is an adhesive. In other applications, the binder is in the form of fibers of low-melt polymer dispersed throughout and entangled within the fabric. These low-melt fibers are melted to wet the knot-forming entanglements and then cooled and solidified to secure the loops and stabilize the fabric. The binder preferably fully penetrates and permeates the interstices between individual fibers in the entanglements of the mat. When employing a liquid binder, the binder is preferably selected to have a sufficiently low viscosity and surface tension to enable it to flow into the untightened (or tightening) entanglements. In the embodiments in which the entanglements are subsequently tightened (such as the loop product shown in FIG. 2), this selected distribution of the fluid binder helps to secure the knots with minimal stiffening of the overall product and without requiring substantial amounts of binder.

In any event, the amount and penetration of the binder should be selected to avoid substantial interference with the desired hook-engaging function of the loops while adequately stabilizing the mat and securing the loops against being pulled from their associated entanglements. For use in applications in which the loop product may come in direct contact with sensitive skin, such as in diapers, the amount and type of binder should also be selected to be biocompatible to avoid skin irritation. Formaldehyde-free binders, for instance, are preferred. As irritation can be aggravated by stiffness, preferably only enough binder to perform the above functions is applied. In some applications, for instance those in which the loop product is directly adhered to a supporting fabric and which does not require substantial fastener strength, the loop product may be provided without a binder.

In important instances, the binder also includes an organic or inorganic fire-retardant, such as antimony oxide, zinc borate, aluminum trihydrate or decabromobiphenyl oxide.

Figure 4A:
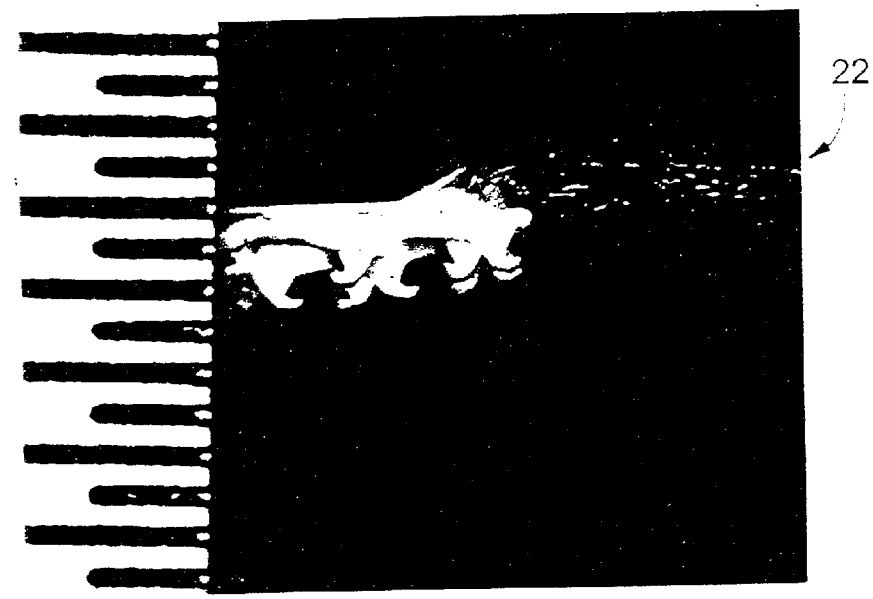
FIG. 4A is an enlarged side view of a hook-and-loop product made by ultrasonically welding a loop product to a hook product.

The specific loop product 12 of FIGS. 1 and 2 includes about one third by weight water-based acrylic binder produced by mixing 80 parts "NACRYLIC" X-4280, a self-reactive acrylic emulsion, with 20 parts "X-LINK" 2804, a self-crosslinking, polyvinyl acetate/acrylate emulsion, both available from National Starch and Resin Company in Bridgewater, N.J. As produced, loop product 12 substantially consists only of the drawn fibers of the thin mat, some of which extend out of the mat to form loops, and the binder. Without any additional backing or laminate, it is strong enough to be handled as a fabric material, and may be applied to surfaces as a closure member by sewing, ultrasonic welding, adhesive, radio frequency welding, or other known attachment means. FIG. 4A, for instance, shows a hook-and-loop product 22 formed by ultrasonically welding a piece of the loop material 12 of FIG. 2 to a piece of CFM-29 hook product. The resulting product 22 can be formed into a closed band by engaging its loops with its hooks.

Figure 6:
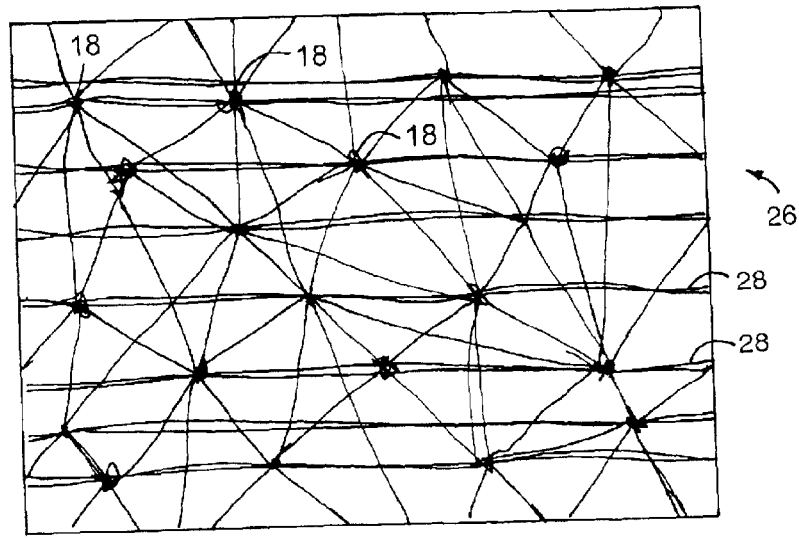
FIG. 6 illustrates a loop material containing longitudinal fibers.

Referring to FIG. 6, another loop fabric material 26 includes, in addition to the drawn, molecularly oriented, randomly laid fibers previously described, continuous robust longitudinal monofilament fibers 28 extending substantially in one direction to augment the tensile strength of the finished fabric in the direction of the strands. For this purpose the diameter of the longitudinal monofilaments is selected to be larger than the barbs of the needles to reduce engagement of the monofilaments by the needles during the needling process. Monofilaments 28 are preferably crimped to enable them to be stretched a limited amount in the machine direction as the fabric is stretched before being stabilized. Alternatively, a stretchable scrim of similarly large fibers or film may be incorporated into the web of fibers to increase tensile strength in both longitudinal and lateral directions.

Figure 4B:
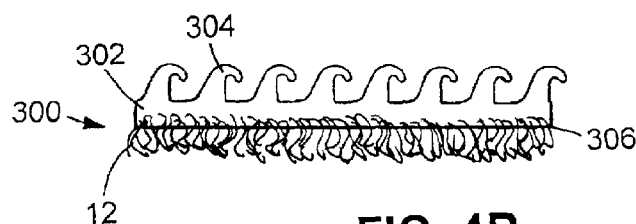
FIG. 4B illustrates a two-sided fastener product formed with loops on one side and hooks on the other.

FIG. 4B illustrates a one-piece fastener product consisting of a lamination of the above-described loop material and molded hook tape. Product 300 has a base 302 with integrally molded hooks 304 projecting from one side and the above-described non-woven loop material 12 secured to the other side. At the interface 306 between the twos layers the plastic from base 302 flows around and entraps some of the fibers of the base web of loop material 12, encapsulating one face of the web in thermoplastic material to form a permanent laminate of the two layers. Because of the extremely light nature of the non-woven material of the invention, care must be taken to only encapsulate the web and to leave the functional loops exposed for engagement with hooks 304. The properties of the non-woven material, the viscosity of the plastic and the pressure in the nip (see FIG. 5) will determine the degree to which the plastic flows into the fibrous network, or put alternately, the degree to which the non-woven will imbed into the plastic. The resulting laminated product is particularly thin and flexible, due in part to the thinness of the loop material.

Figure 5:
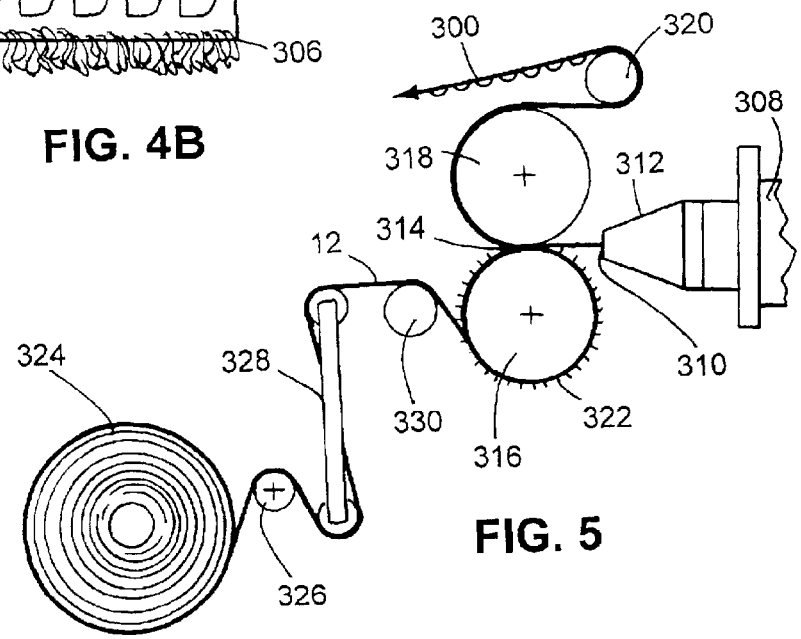
FIG. 5 illustrates a machine and process for forming the product of FIG. 4B.

The product of FIG. 4B may be economically formed by the process and apparatus illustrated in FIG. 5. Extruder barrel 308 melts and forces the molten plastic 310 through die 312 into the nip 314 between base roller 316 and cavity roller 318 containing cavities to form the hooks of a strip fastener of the well known hook and loop type. The strip fastener material formed in nip 314 travels around the periphery of cavity roller 318 and around stripping roller 320, which assists in pulling the finished product 300 from the cavity roll, and from there to a windup device, not shown.

While many methods of feeding sheet material to the forming section of the hook forming device are possible, FIG. 5 illustrates a device particularly well adapted to that purpose. By introducing loop material 12 into nip 314 at the same time molten plastic 310 is forced into the nip, the loop material will bond intimately with the fastener to become an integral part of the structure of the strip fastener. Optionally, a set of pins 322 at the edges and around the periphery of backing roller 316 carry the loop material 12 into nip 6 in a flat, unwrinkled state. To assure proper tensioning and alignment of the secondary sheet material, a roll 324 of loop material 12 is mounted on a let off device and threaded around diversion roller 326 into a web straightening device 328, well known in the art as typically sold by the Fife Manufacturing Company which assures that the web of loop material is centered as it is fed onto backing roller 316 around scroll roll 330, which has ribs of elastomeric material to firmly grip the sheet and impinge it against backing roller 316 and onto pins 322. Pins 322 and roller 316 deliver the web into nip 314 along with molten plastic 310. As molten plastic 310 is forced by the pressure imposed upon it by the narrow space of nip 314, it flows into cavities in cavity roller 318 and also into pores in the adjacent face of the loop material being carried by backing roller 316. In this way the loop material is intimately joined to the base of the forming hook fastener tape to form laminated product 300.

For more detail about proper operation of the apparatus of FIG. 5, the reader is referred to U.S. Pat. No. 5,260,015 to Kennedy, et al., which discloses laminates made with heavier loop materials.

The very low thickness and stiffness of the above-described loop material, along with its low cost and good closure performance, make it particularly useful for many touch fastener and filtering applications. Many examples of such uses are described in co-pending U.S. patent application Ser. No. 08/922,292, the disclosure of which is incorporated herein by reference as if fully set forth.

One of the underlying principles embodied in the formation of self-erecting loop trees is that pulling on a tangled bunch of fibers will form knots. This phenomenon is true with regard to continuous fibers (as any fisherman knows) as well as to bunches of short fibers tangled sufficiently to form a coherent mass. Simply stretching a tangled mass of fibers is insufficient to form an adequate number of erect loop trees, however. The formation of an erect structure of the proper height, as shown in FIG. 3A for instance, involves the tightening of adjacent fibers within the plane of the base of the mat about multiple tree-forming fibers at two spaced-apart points along each tree-forming fiber, which themselves remain untightened between such spaced-apart points.

Figure 7A:
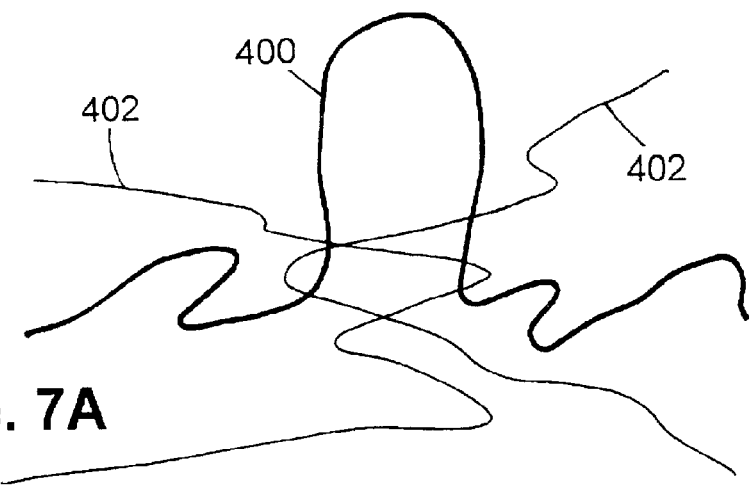
FIGS. 7A–7C sequentially illustrate the formation of a loop tree.
Figure 7B:
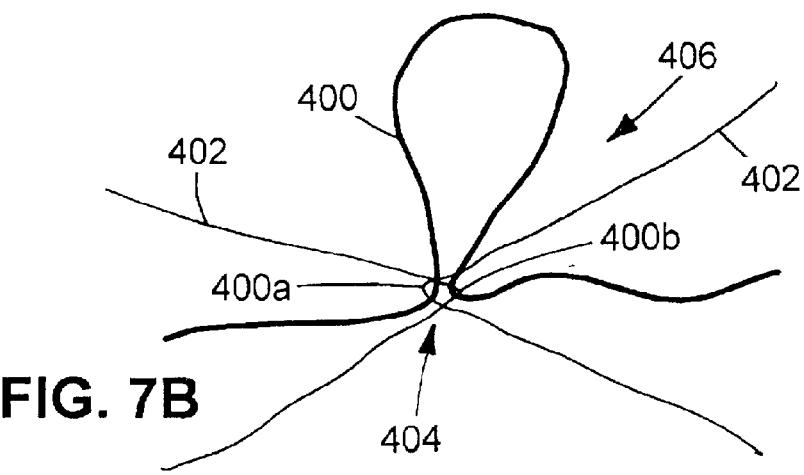
Figure 7C:
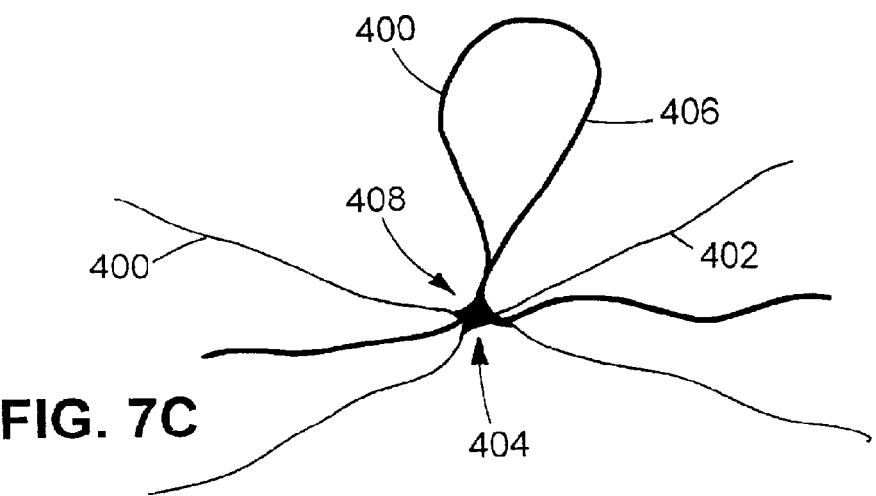

FIGS. 7A–7C illustrate this tree-forming sequence. For clarity, only one tree-forming fiber 400 is shown (in bold for distinction), and only two tightening base fibers 402 are shown. Preferably, an average of at least three or four tree-forming fibers will be drawn together at any given knot to form a single trunk. Referring first to FIG. 7A, all fibers are initially slack. As the fibers are pulled taut (FIG. 7B), fibers 402 tighten about fiber 400, drawing together spaced-apart points 400*a* and 400*b* into a tight entanglement 404 at the base of the loop structure 406 formed by the segment of fiber 400 between points 400*a* and 400*b*. The wicking of binder 408 into the interstices between fibers in knot 404 (FIG. 7C) adds rigidity to the trunk of the structure and its connection to the base. Again, with multiple tree-forming fibers 400 drawn together at a common entanglement 404, this process forms a standing loop tree with multiple extended loops.

FIGS. 8 and 9 illustrate one apparatus and method for producing the above-described loop material. The apparatus includes a feeder 110 (with, e.g., bale breakers, blender boxes or feed boxes), which feeds staple fibers of a desired length of drawn fibers to carding machines 112. The carding machines 112 card the staple fibers to produce carded webs of fibers 114 which are picked up by the takeoff aprons 116 of cross-lappers 120. The cross-lappers 120 also have lapper aprons 118 which traverse a floor apron 122 in a reciprocating motion. The cross-lappers lay carded webs 114 of, for example, about 12 to 18 inches (30 to 45 cm) width and about one inch (2.5 cm) thickness on the floor apron 122, to build up several thicknesses of criss-crossed web to form a batt 124 of, for instance, about 90 to 120 inches (2.3 to 3.0 m) in width and about 4 inches (10 cm) in thickness. During carding, the material is stretched and pulled into a cloth-like mat consisting primarily of parallel fibers. With nearly all of its fibers extending in the carding direction, the mat has some strength when pulled in the carding direction but almost no strength when pulled in the carding cross direction, as cross direction strength results only from a few entanglements between fibers. It is important to note that the carding direction is not the machine direction of the finished product. During crosslapping, the carded fiber mat is laid in an overlapping zigzag pattern, creating batt 124 of multiple layers of alternating diagonal fibers. The diagonal layers, which extend in the carding cross direction, extend more across apron 122 than they extend along its length. For instance, we have used batt which has been crosslapped to form layers extending at anywhere from about 6 to 18 degrees from the cross direction of the finished product. The resultant crosslapped batt 124, therefore, has more cross direction strength (i.e., across apron 122) than it has machine direction strength (i.e., along apron 122). Note that the machine direction of the final product is in the same sense as the direction along apron 122. Batt 124 has little machine direction strength because the fiber layers are merely laid upon one another and are in no way woven together. The material properties and the manufacturing process can be affected by the crosslapping angle. A steeper angle may balance the cross and machine direction strengths, which may affect fastener performance and the ease of manufacturing. With more machine-directional crosslapping, in some cases the initial machine direction stretch described below may be eliminated while still obtaining a useful product.

In preparation for needling, batt 124 is gradually compressed in a tapered nip between floor apron 122 and a moving overhead apron 138 to reduce its thickness to about one inch. A relatively thin, low density batt can thus be produced.

Needling of batt 124 is performed in multiple, sequential needling stages in order to provide a very high density of needle penetrations without destroying the low density batt. In the presently preferred method felting needles are employed having fiber-engaging barbs on their sides. Needle punching gives the batt cohesion. The needle barbs pull fibers from one layer of the batt through other layers, entangling the fibers from different layers that are oriented in different directions. The resulting entanglements hold the batt together.

From floor apron 122, the batt is passed to a first needle loom 140 with two needling stations 142 and 144 having rows of notched (i.e., barbed) needles. Needling station 142 needles the batt of staple fibers from its upper surface at a density in the range of 100 to 160 punches per square inch (15 to 25 per square cm). In this embodiment, the batt was needled at a density of 134 punches per square inch (21 per square cm). Subsequently, needling station, 144 needles the once-needled batt a second time, with needles which penetrate the batt from its upper surface at a density in the range of 500 to 900 punches per square inch (78 to 140 per square cm) to produce a needled batt 146. In this example, the second needling is at a density of 716 punches per square inch (111 per square cm). We refer to the operation of loom 140 as the first needling stage. Additional information on needling processes can be obtained from the Association of the Nonwoven Fabrics Industry (INDA) of Cary, N.C., which publishes the *INDA Nonwovens Handbook*.

After the first needling stage, needled batt 146 is passed between drive rolls 148 and into a J-box accumulator 150 which, besides holding a bank of-batt to accommodate variations in processing rates, allows the needled batt to relax and cool before entering the second needling stage. Alternatively, the needled batt 146 may be spooled after the first needling stage, with subsequent operations performed on a second line. If materials and conditions allow, the needled batt may be passed directly from the first needling stage to the second needling stage without accumulation, but care should be taken to ensure that the batt is sufficiently cool and relaxed to withstand the second needling stage.

As a result of the needle punching, the fibers of the batt become highly randomized and chaotic. However, the underlying pattern of alternating diagonals remains unchanged, although obscured.

From J-box accumulator 150, needled batt 146 is pulled through a guider/spreader 152 (of, e.g., the one-over-two configuration) to properly apply light tension to the batt as is customary for needling, without significant stretching of the batt. It then passes through a second needle loom 154 for a second needling stage. The operation of this second stage is referred to "super needling", as it is a very dense secondary needling operation and produces many loops of substantial loft. Loom 154 has a single needling station 156 in which needled batt 146 is needled from the lower side to produce high-loft loops extending from the upper side. To produce such loops, the sharp tips of the notched needles of loom 154 are extended a substantial distance (e.g., about ¼ inch or 6.3 mm) beyond the thickness of the batt in the opposite direction as the needles of the first needling station, pushing individual fibers away from the bulk of the batt to form upstanding loops. When the needles retract, the loops remain. The loops may be formed of fibers which originally lay on the opposite side of the batt, or from fibers drawn from the middle of the batt. In either case, the needles drag fibers out of the batt and leave them extending from the bulk of the batt as loops which give one side of the super-needled batt a fuzzy appearance.

This super-needling process does not require special needling bedplates or supporting brushes into which the needles extend, such as are employed in structured or random velour looms, although such techniques may be employed to advantage, e.g., where large loops are desired for use with large hooks. The super-needling is primarily characterized as an extremely dense needling, on the order of about 1000 to 2000 punches per square inch (155 to 310 per square cm), or preferably about 1400 punches per square inch (217 per square cm). Standard barbed needles are employed, such as triangular section 15×18×42×3 C222 G3017 felting needles from Groz-Beckert. During this secondary needling operation, individual fibers of the batt are pushed through the loop side of the batt to produce loose, relatively lofty loops. Together, these loops give the loop side of the, super-needled batt a fuzzy appearance and feel. Too much extension of the individual loop fibers at this point can cause them to break during subsequent stretching, so the distance the needles extend through the batt is selected in consideration of the denier and tenacity of the fibers used. We have found that extending the needles about ¼ inch (6.3 mm) beyond the batt works well for 6 denier fibers with a tenacity of about 3.5 grams per denier.

In one embodiment, illustrated in FIG. 10, needle loom 154 has an additional, second needling station 158. After producing high-loft loops extending from one surface, the batt is super needled in the other direction to produce loops extending from its other surface, such that both sides have extended loops.

Figure 11:
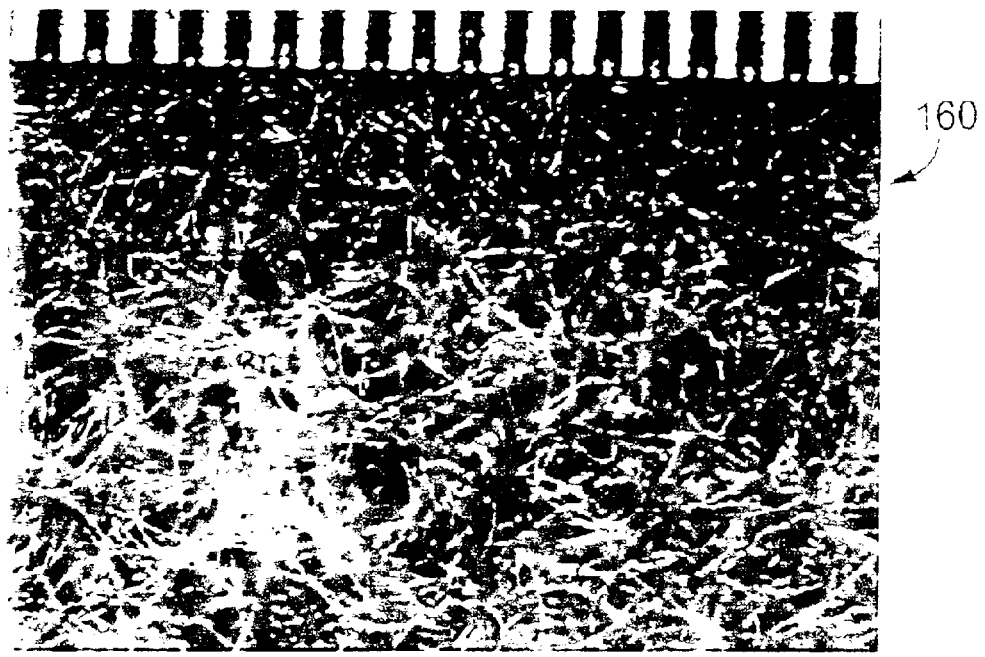
FIGS. 11 and 11A are plan and side views, respectively, of a batt of needled material after the second needling stage.

After leaving loom 154, super-needled batt 160 is split into two running 45 inch (114 cm) widths and spooled on rolls 162. As shown in FIG. 11, the fibers of batt 160 have been entangled by the needle punching process to create loose entanglements throughout the batt. At this stage, the batt is not an acceptable loop product for many hook-and-loop fastening applications, as the individual loops may be relatively easily pulled away from the batt and are not well anchored at the entanglements.

Figure 11A:
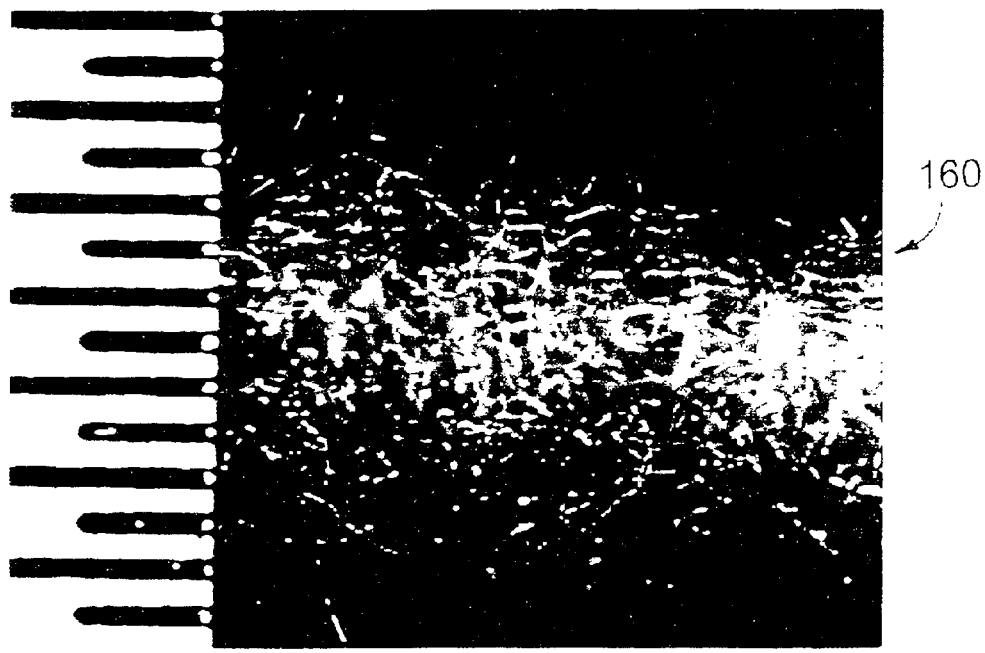

After super-needling, the loop definition, see FIG. 11A, on the working side of the batt is also not as distinct as it can be after the stretching that is employed to produce products with loop trees. This structural difference can be seen by comparing FIGS. 11, 11A with FIGS. 2 and 3, for instance.

In another embodiment (not illustrated), the second needling stage is omitted. Instead, needle looms 142 and 144 of the first needling stage (FIG. 9) are configured to super-needle the batt in both directions. Loom 142 needles the batt from the top at a rate of 254 punches per square inch (39 per square cm), with the needles penetrating the batt and extending through the bottom of the batt a distance of 10.2 millimeters. Loom 144 then needles the batt from the bottom at a rate of 254 punches per square inch (39 per square cm), with the needles penetrating the batt and extending through the top of the batt a distance of 7.1 millimeters to form loops on the top side of the batt. The needles of loom 144 tend to take fibers that have been pushed through the bottom of the batt by the needles of loom 142 and force them back up through the batt in the formation of topside loops. Although this process results in a relatively small number of loops on the bottom of the finished product, due to the first needling of loom 142, the resulting product has been found to be useful for some applications. The needling density, speed, and penetration of looms 142 and 144 may be varied to produce a product with substantially no backside loops, or with hook-engageable loops extending from both sides.

The batt following super needling has a fair amount of loft and resiliency, with the loops and other fibers of the batt forming loose, gentle arches between entanglements. At this point the batt is very flexible, and the density of fibers gradually decreases away from either side of the material. At first glance, it can be difficult to tell which side has been super-needled, if only one side has been subjected to that action. Batt 160, in this example, has an overall thickness, including loops, of about 3/16 inch (4.8 mm) and a weight of between about 2 and 4 ounces per square yard (68 and 135 grams per square meter).

Figure 12:
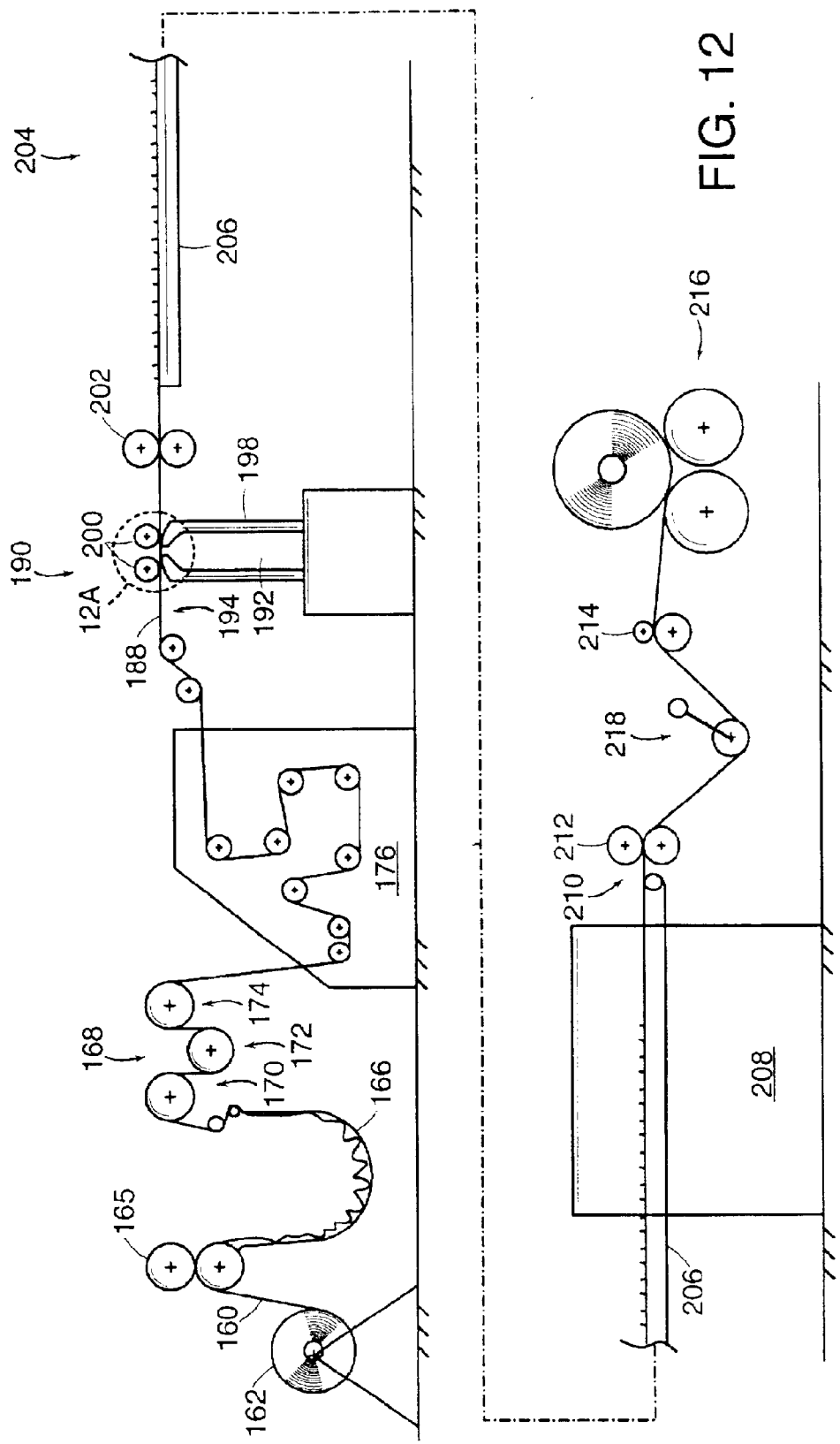
FIG. 12 is a schematic view of an apparatus for stretching and stabilizing a nonwoven material.

Referring to FIG. 12, a spooled length of super-needled batt 160 is spooled from roll 162 by drive rolls 165 and into a J-box accumulator 166, allowing roll 162 to be replaced and the batt spliced without interrupting further processes. The J-box also allows the batt to recover from any elastic deformation caused by the spooling process. Batt 160 is pulled from accumulator 166 through a guider 168 to center the batt in the cross-machine direction. Guider 168 includes three rolls in a two-over-one configuration. The first and second rolls 170 and 172 have left and right herringbone pattern scroll surfaces originating at the center of the roll that, being slightly overdriven, urge any wrinkles in the batt toward its edges to remove them. The third roll, roll 174, is a split braking roll to controllably tension either half of the batt to guide the fabric to the left or right as desired.

From guider 168 the batt passes through a tension controller 176 that maintains a desired tension in the batt through the subsequent binder application process. Controlling the difference between the speed of tension controller 176 and downstream drive rolls 202 applies a desired amount of machine direction stretch to the batt prior to cross-machine stretching. In some cases, no substantial machine direction stretch is purposefully applied, any noted machine direction lengthening being due only to minimal web processing tension in the supply batt. In other cases, machine direction stretch is purposefully induced by running drive rolls 202 faster than tension controller 176.

In the embodiment in which batt 160 has been super-needled to produce loops extending from only its front side 188, batt 160 is next passed through a coating station 190 in which a foamed, water-based adhesive 192 (i.e., a water-based adhesive, whipped to entrain air) is applied to the back side 194 of the batt across its width.

Figure 12B:
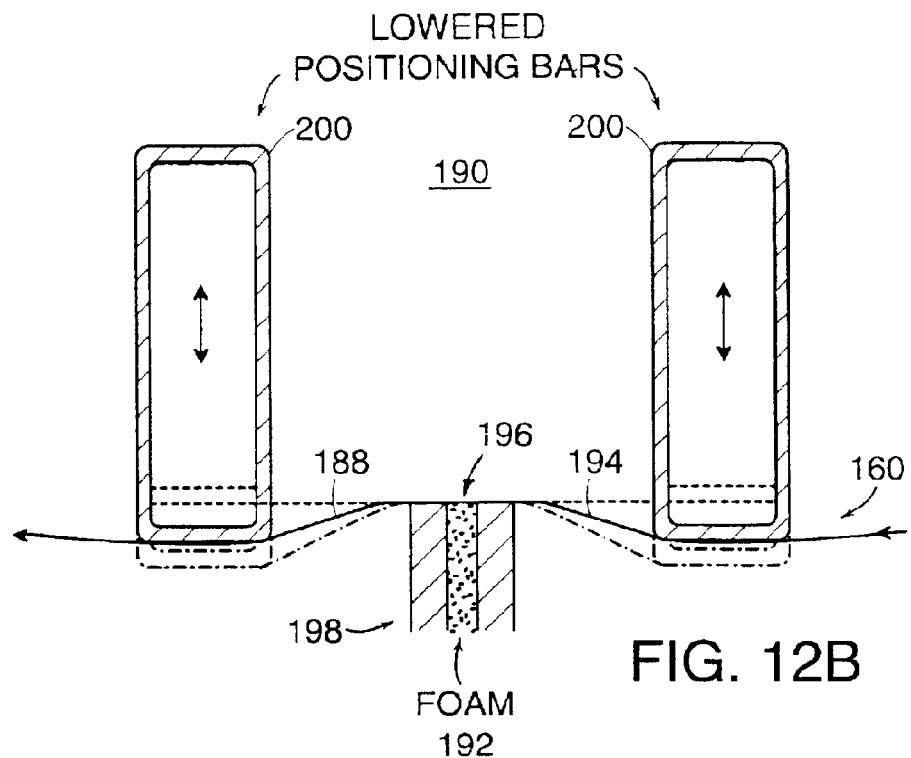
FIGS. 12A and 12B are enlarged views of area 12A in FIG. 12 under two different conditions of operation.
Figure 12A:
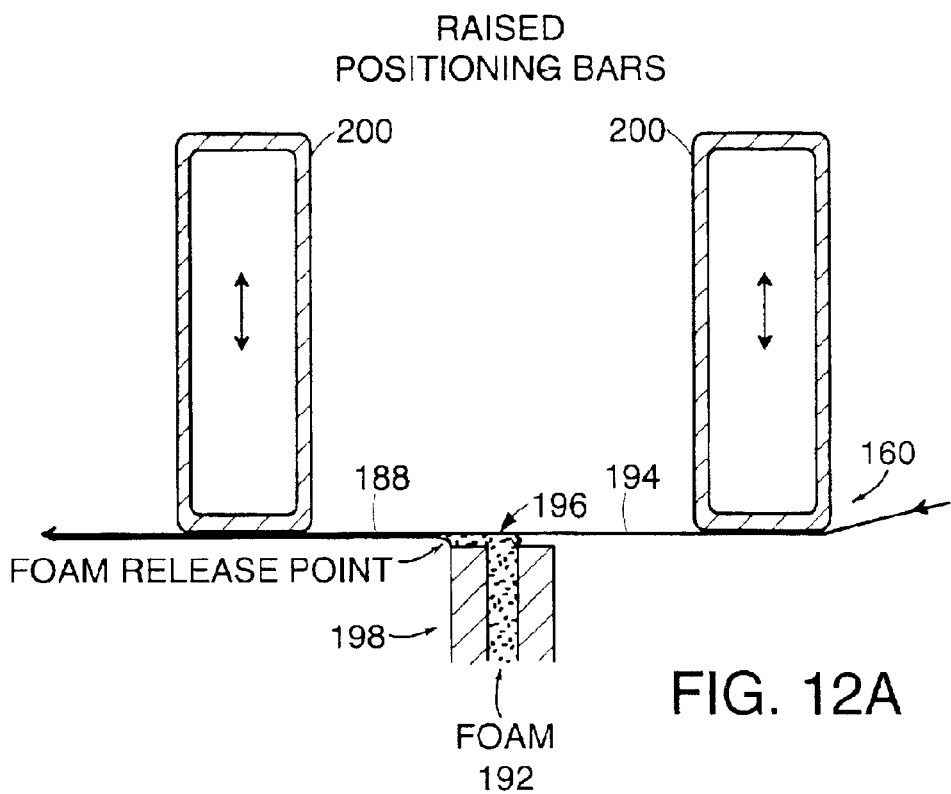

Referring also to FIGS. 12A and 12B, the foamed liquid adhesive is pumped at a controlled rate through a long, narrow aperture 196 in the upper, surface of the applicator 198 as the batt is wiped across the aperture, thereby causing the adhesive to partially penetrate the thickness of the batt. Positioning bars 200, on either side of aperture 196, are raised (FIG. 12A) and lowered (FIG. 12B) to control the amount of pressure between batt 160 and applicator 198. The depth of penetration of the adhesive into the batt is controlled (e.g., by the flow rate and consistency of adhesive 192, the speed of batt 160 and the position of bars 200) to sufficiently coat or penetrate enough of the fiber entanglements to hold the product in its final form, while avoiding the application of adhesive 192 to the loop-forming fiber portions of the front side 188 of the batt. The foaming of the liquid adhesive before application helps to produce an even coating of the back side of the batt and helps to limit penetration of the fluid adhesive into the batt. After the semi-stable foam is applied it has a consistency similar to heavy cream, but the bubbles quickly burst to leave a liquid coating that flows as a result of wetting and surface tension, into the tightening fiber entanglements. Alternatively, the foam may have a thicker consistency, more like shaving cream, to further reduce the penetration into the batt and form more of a distinct resinous backing. A non-collapsible (i.e., stable) foam of urethane or acrylic, for instance, is useful to produce a radio frequency-weldable backing which functions as a water barrier. Such a product has particular application to disposable garments and diapers.

It is important that the binder (e.g., adhesive 192) not interfere with the loop-forming portions of the fibers on the front side 188 of the batt. It is not necessary that the knot bases be completely covered by binder; it is sufficient that they be secured by the binder in the finished product to stabilize the fabric against significant further stretching and to strengthen the bases of the loops. Preferably, the binder is at least partially in liquid form to wick into the entanglements before and while they are subsequently tightened during stretching. The capillary action of the liquid binder is such that examination of the finished product shows that the binder is almost exclusively at the knots of the web (at the base of the loops, for instance), and therefore does not tend to adversely affect either the functionality of the free-standing loops or the flexibility of the web.

After leaving coating station 190, the material is subjected to stretching in the plane of the web. In the presently preferred case the web is wound through variable speed drive rolls 202 and onto a tenter frame 204 for cross-machine stretching (i.e., stretching in the cross-machine direction). The speed of drive rolls 202 is adjustable, with respect to both tension control 176 and the rails 206 of the tenter frame, to cause a predetermined amount of machine direction stretch in the batt, either between tension control 176 and drive rolls 202, or between drive rolls 202 and frame rails 206, or both. In some embodiments no permanent machine direction stretch is applied, but the batt is nevertheless held in tension to control adhesive penetration and maintain proper frame rail pin spacing. In other embodiments the batt is generally stretched, in total, between about 20 percent and 50 percent in the machine direction before tentering.

As it enters tenter frame 204, the 45 inch wide batt 160 is engaged along its edges by pins of frame rails 206 that maintain the machine-direction dimension of the material as it is stretched in the cross-machine direction. The spacing (of, e.g., about 3/16 inch or 4.8 mm) between adjacent pins is maintained throughout the length of the tenter frame, such that no additional machine-direction stretch is applied. Due to the needling, batt 160 should have enough tensile strength to be properly engaged by the rail pins and withstand the subsequent cross-machine stretching.

Tenter frame 204 has a tapered section where the rails 206 separate at a constant, adjustable range rate over a machine-direction length of about 10 feet (3 meters) to a final width which can range from 45 inches (114 cm) to about 65 to 69 inches (165 to 175 cm). This equates to a cross-machine stretch, in this particular embodiment, of about 50 percent. In general, to take advantage of the economics that can be realized according to the invention, the batt should be stretched to increase its area by at least about 20 percent (we call this "percent areal stretch"), preferably more than about 60 percent areal stretch and more preferably more than about 100 percent areal stretch, to increase the area of the product while tightening the binder-containing entanglements of the batt that contribute to improvement in the strength of anchorage of the individual loops. We have found that in some cases the super-needled batt can be stretched, by employing the above method, at least 130 areal percent or more and provide very useful hook-engaging properties. The more the stretch, the greater the overall yield and the lighter in weight the final product. Even greater overall cross-machine stretch percentages can be employed, for instance by using multiple tentering stages in situations wherein the batt is constructed to withstand the stretch and still be able to reasonably engage hooks. In one instance, the super-needled batt described above was stretched from an initial width of 45 inches (114 cm) to 65 inches (165 cm), softened (by adding a softener), slit to a 45 inch (114 cm) width, stretched a second time to a 65 inch (165 cm) width before applying a binder, and still had useful, hook-engageable loops. In some cases final product widths of 6 to 8 feet (1.8 to 2.4 meters) or even much more can be achieved.

In one embodiment, the non-woven web starting material used to manufacture the loop component is a fairly dense, needle punched, non-woven web of fibers lying in an apparently chaotic and tangled manner. One side, the "fuzzy side", has an excess of large, loose loop fibers created during a second needle punching process. The web is first stretched to 130 percent of its initial length in the machine direction. This stretching results in necking—the material narrows to 80 percent of its initial width, from 45 inches (114 cm) to 36 inches (91 cm). It is then coated with a binder. Next, it is stretched to 175% of its necked width, from 36 inches (91 cm) to 63 inches (160 cm). During this process the material becomes much more sparse, with spider-like clusters of fiber (see bases B of FIG. 2B) serving to anchor the loop. The mechanism by which this change occurs relates to the method by which initial/nonwoven web is manufactured.

Figure 14A:
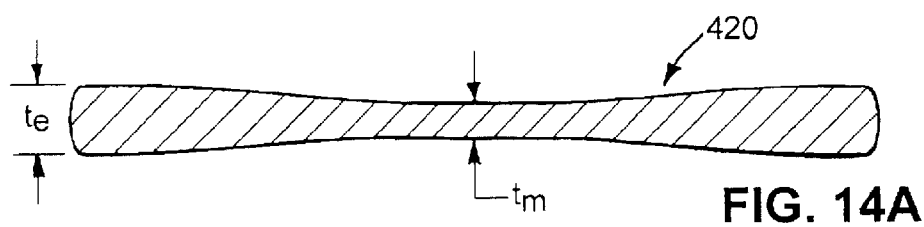
FIGS. 14A–14C are transverse cross-sections through a fiber batt that illustrate, sequentially, stretching of a batt of non-uniform thickness slit from a needled batt.

Referring to FIG. 14A, a cross-lapped and needled batt 420 generally has a smaller thickness ($t_m$) along its center-line than at its longitudinal edges ($t_e$), due to the interrelation of motions of conveyor, carded webs and cross-lappers during cross-lapping, which tend to create thicker batt edges (i.e., edges having a greater basis weight than the center of the batt). The edge thickness may be 30% or more greater than the mid-thickness, and the basis weight of the batt generally varies across its width in proportion to its thickness.

Figure 14B:
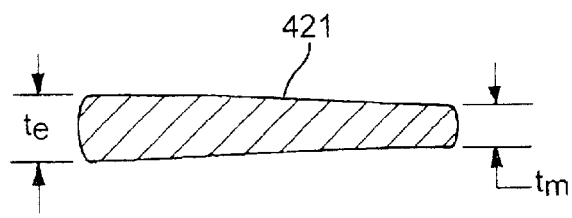
Figure 14C:
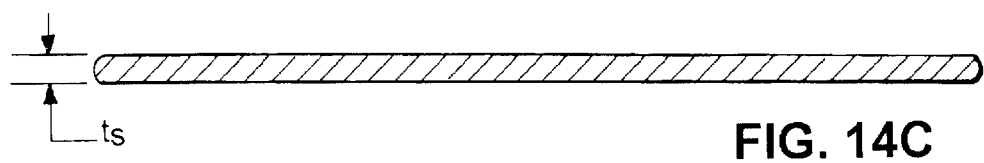

By taking such a variable-thickness batt, slitting it down its centerline into two widths 421 (of, for instance, 45 inches each in width), one of which is shown in FIG. 14B, and then stretching each width 421 to a final width about equal to the width of the original needled batt, as shown in FIG. 14C, a useful loop product of uniform thickness is formed. The variation in thickness across the width of the slit batt is diminished as it is stretched, such that the final stretched web thickness ($t_s$) is substantially uniform across the width of the finished product. We believe that the mechanism for this thickness equalization is that the base fibers of the thinner regions of the batt are tightened first, thinning the thinner regions all the more, and then, when further stretching of the thinner regions is limited by their tightened fibers, the thicker regions are stretched until a matrix of taut fiber portions is formed within them as well. In effect, the material is "drawn" in the cross-machine direction, as tensioning begins in the thinner areas of the batt and migrates or propagates to and through the thicker areas. We have found that the distribution of loop structures across the width of the finished product is substantially uniform, even when starting with an uneven batt.

The amount of needling, the starting basis weight, and the stretchability of the batt are all related. Within a range of basis weight and needling density useful for creating a stretchable web, increasing either the basis weight of the starting batt or the needling density will decrease the amount of stretch that can be applied to the needled batt. As is known in the art, there is a minimum basis weight required for effective needling, below which an insufficient number of entanglements will be formed by the needling to produce a coherent web which can be handled without falling apart. At the other end of the spectrum, too high of a basis weight can result in needle breakage and/or fiber breakage during needling. To produce the very light, thin loop material enabled by the invention, the basis weight of the starting batt and the needling density should be selected to permit a fair amount of stretch of the needled material, as it is the stretching that thins the needled product and increases its yield. In other words, if the needled product is to be stretched, the needling process should leave a substantial proportion of the base fibers slack, and their entanglements loose.

When loop material formed of a highly diagonal crosslapped batt is stretched in the machine direction, it is observed that little tension is placed upon the constituent fibers. This is because the vast majority of the fibers run in a diagonal direction that lies close to the cross machine direction. Applying machine direction tension tends to increase the angles at which the diagonals lie (i.e., move them toward a 45 degree angle with the machine direction). They become steeper, or are turned to a degree toward the machine direction, much like the angles of the legs on a folding chair grow steeper when the chair is opened. And just as the leg base of a folding chair gets narrower as the chair gets taller, so does the material tend to neck and lose width as it is stretched. This is evidenced by breaking a piece of such material in the machine direction: the fibers do not break, they merely pull apart from each other. Because little tension is put on the fibers until they are nearly parallel, a mere 30 percent stretch does not disturb the chaotic arrangement of the fibers and little change can be seen under the microscope. Even though the fibers are re-orienting, the arrangement looks no less chaotic, since the fibers themselves are never brought under enough tension to straighten them out.

The second stretch of the above embodiment, performed in the cross machine direction, produces drastic changes. Though somewhat more angled as a result of the first stretch, the fibers still extend more in the cross machine direction than in the machine direction. The fact that the fibers are oriented closer to cross machine direction means that a smaller elongation is required before the fibers are close enough to the cross direction to experience tension. Tension, when applied, causes the fibers to try to straighten themselves out and re-orient into the cross machine direction. If the web were not previously needle punched, the material would probably lose all cohesion at this point. However, the needle punching of the web causes fibers from different layers with different orientations to entangle one another. Because of these entanglements, the fibers cannot straighten. As cross machine tension is applied the entanglements tend to bunch together to generate knots that resemble "spiders" as they have a core with many taught legs emanating from the core in different directions. Each spider forms at a point where a needle caused an entanglement of multiple fibers, which tried to pull apart during the cross direction stretch. The bunching of the entanglements gives them the spider like appearance. Each loop of the fuzzy side corresponds to a point where a needle was punched through; consequently, after the cross direction stretch each fuzzy side loop lies at the center of a corresponding spider-like knot. This was seen in one experiment where the functional loops (i.e., the outer region of the fuzzy side) of the product were colored purple. All of the purple in the colored product was visible at the centers of the spiders formed at the bases of the loops. On the other hand, when the non-fuzzy side of the fabric was colored, no gathering of color at the center of the spiders was observed. Only the fuzzy side, functional loops corresponded to needle punches, and only these loops were observed to have spiders form around them. It is believed that the presence of the loop and its corresponding entanglement is largely responsible for the formation of the spider or knot. The fact that a loop is pulled through the web means that there is now a vertical fiber (i.e., a fiber extending out of the plane of the web) around which the horizontal fibers of the web entangle. Thus most loops in the finished loop tape have a spider at their base, which provides increased strength for anchoring the loop.

Stretching the experimental, purple-looped sample past the point at which the loops are of maximum height tended to draw the purple tinted loops back into the plane of the web. The greater the stretching, the smaller the loops grew, until finally they began to pull out of their entanglements. As this happened, the spider that had formed around them disappeared and the entangled fibers straightened and sank back into the web. With increased stretching, after many loops are drawn back and their entanglements vanish, the material loses its cohesion, the fibers slide past one another, and the material parts.

From this examination, it appeared that the material is stronger in the cross machine direction, attributed to the fact that the carded fabric is cross-lapped at an angle closer to this direction. By changing the carding angle progressively away from the cross-machine direction, more strength in the machine direction should be achievable. Also, machine direction stretching tends to re-orient the fibers towards the machine direction. However, since they begin close to cross direction, the mere 30 percent elongation that the material undergoes in the above-described longitudinal stretching is insufficient to place enough tension on the fibers to straighten them or to cause spiders or knots to form. However, machine direction stretching is considered important for highly cross-directional crosslapped batts, which would otherwise have a lay which is too cross-directional for a uniform cross direction stretch to be achieved; in that case the fibers are so close to cross-directional that they do not entangle as significantly, nor are they properly spaced in the final product. Instead, they remain very near to each other and nearly parallel. When the spiders do form in such instances, they are elongated in the cross direction and very close together, and the end material is much more dense.

Because in the above-described embodiment the fibers are already more cross-directional than machine-directional, and because the cross direction stretch applied is greater, the fibers are placed under tension during cross direction elongation. Fibers entangled during needle punching tend to clump together, and as the fibers tend to straighten, these entanglements form spider-like radial patterns of fibers.

It was also noted that spiders form at the location of functional loops created by deep needle punching, the fibers of which have been drawn through some or all of the web. Consequently, the loop fibers entangle the other fibers and form spiders. This means that in the finished product, the loops have spiders at their base, locking the loop fibers into the web.

Another way of saying this is that the "loop trees" (see FIG. 3B), which do not distinctly appear in the pre-stretched batt, obtain their final form as fibers of the ground portion of the web are pulled and the entanglements beneath them are tightened during stretching to form knots. As the batt is stretched, the tension in the taut fibers of the web forces some of the loop trees to stand erect, such that the overall thickness of the stretched batt (with functional loops) can actually be greater than the unstretched batt. To extend the horticultural analogy, the homogeneous thicket of the loop surface of the unstretched batt becomes the orchard of spaced clusters of the stretched product. Although the loop trees or loop formations correspond to locations where the batt was punched during super-needling, the resulting "orchard" of loop formations does not exhibit the same ordered pattern, after the web is stretched, as might be anticipated by the pattern of punches of the needling process. We believe that the arrangement of loop formations is randomized during the stretching process, as distances between entanglements change as a function of the properties, direction and number of the fibers connecting various nodes. The resulting product has no apparent order to the arrangement of loops extending from its surface.

Despite the relatively wide loop spacing that is achieved, the loops, after curing of the binder, are found to be so strongly anchored and so available for engagement by the hooks, that a web unusually treated according to these techniques can perform in an excellent manner despite having a gossamer appearance.

Referring back to FIG. 12, while the stretched batt is held on frame rails 206 in its stretched condition it is passed through an oven 208 in which the product is heated to dry and cross-link acrylic binder 192 and stabilize the dimensional integrity of the batt. Oven 208 is essentially a convection drier with air venturi nozzles which blow hot air up into and down onto the web to evaporate some of the water of the adhesive. In this example, the heating time and temperature are about one minute and 375 degrees F. (190 degrees C.), respectively. In some embodiments (not shown), the batt is retained on frame rails 206 for secondary coating passes through additional coating stations and drying ovens, thereby building up a desired laminate structure for particular applications.

In another embodiment, hook-engageable loops are formed on both sides of the web by needling, by the super-needling techniques acting on staple fibers that have been described, or by other known techniques. After forming the loops the web is passed through a bath of binder. In some cases, where the loops are relatively stiff and the binder is of suitably low viscosity, after removal from the bath the binder drains from the loops and the loops, by their own resiliency and stiffness resume their free-standing stance while capillary action retain the binder in the center of the fabric. The web is then subjected to stretching and curing as above.

In other instances, as where the loop material is less stiff, auxiliary means are employed to remove excess binder after passing through the bath, as by passing the fabric through a nip of squeeze rolls, or by subjecting both sides of the fabric to an air knife, or by blotting followed, in each case for instance by blowing air or otherwise loosening the loops and causing them to stand upright.

Other embodiments carrying hook-engageable loops on one or both sides, and incorporating heat-fusible binder fibers or other heat-fusible binding constituents, are bonded by non-contact means such as by blasts of hot air directed at both sides of the fabric at temperatures sufficient to melt the heat-fusible binding material and lock the fabric structure in its stretched condition.

Heat fusible fibers or other-material colored black or otherwise adapted to absorb radiant heat, may be activated by radiant heaters to bind the ground portion of the fabric following stretching. Care must be taken, in such instances, to avoid mitigation of the engagement properties of the free-standing loops.

Referring back to FIG. 12, the stretched batt exits oven 208 still attached to the pins, and is then pulled from the pins by a de-pinning device 210 and a pair of drive rolls 212. The finished, wide batt is then slit, if desired, into appropriate multiple widths by a slitter 214 and spooled on a driven surface winder 216. A dancer 218 between drive rolls 212 and slitter 214 monitors the tension in the batt to control the speed of winder 216. Slitter 214 can also be used to trim off the edges of the batt that include the material outboard of the frame rails through the tenter frame. Optionally, the finished batt can be brushed before or after spooling to disentangle loosely-held loop fibers to improve the consistency of the closure performance between the first and subsequent engagements with a hook product.

Alternatively, heated rolls, "hot cans" or platens may be employed to stabilize the back side of the fabric in its stretched condition. This embodiment does not require a coating or adhesive when using thermoplastic fibers, as the fibers are locally fused together by heat. Cooled rolls engage the loop side of the fabric during stabilization, to prevent damage to the hook-engageable loops.

It will be understood that the above-described stretching technique can be employed to advantage on other stretchable, loop-defining non-woven webs. Thus, in its broadest aspects, the invention is not to be limited to the use of needled webs. Webs formed by hydro or air current entanglement can, for instance, be employed.

Figure 13:
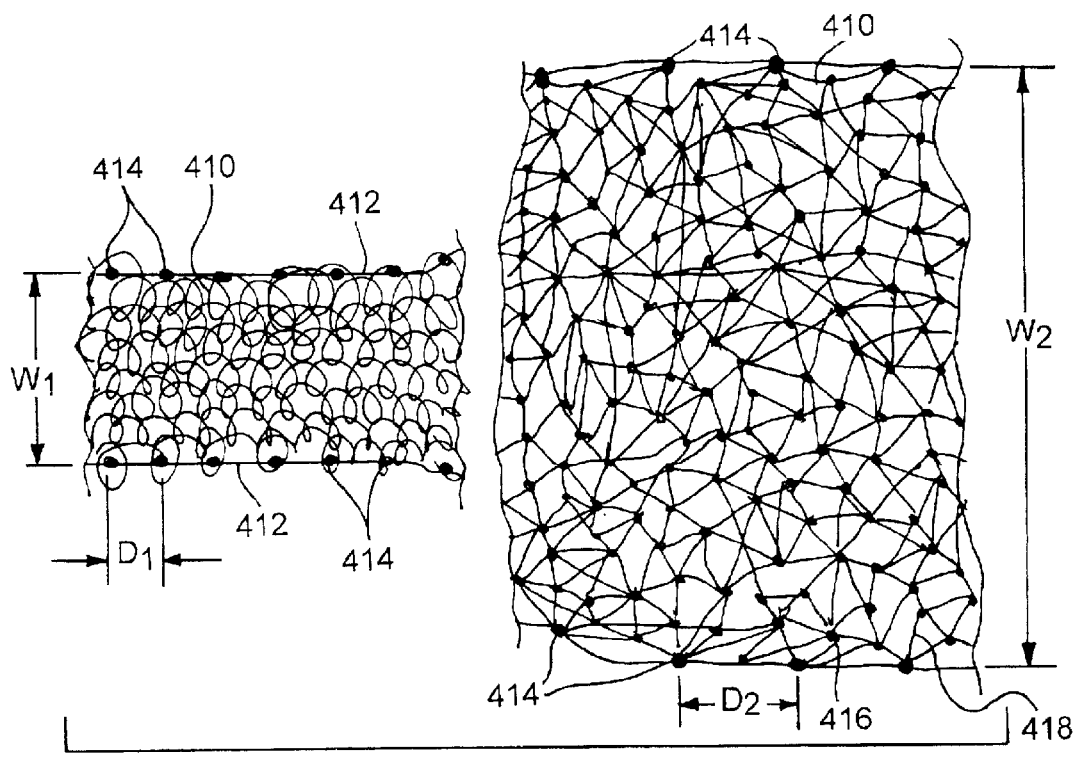
FIG. 13 is a top view illustrating another process for forming a stretched, entangled fiber batt.
Figure 13A:
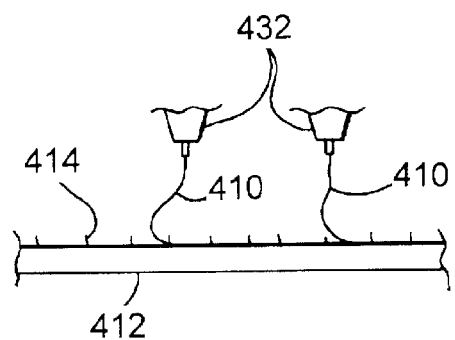
FIG. 13A is a side view of the process illustrated in the left half of FIG. 13.

FIGS. 13 and 13A illustrate a method of forming an entangled, stretched web from a spun fiber mat. A continuous base fiber 410 is spun onto a supporting surface between tenter frame rails 412, forming overlapping coils of spun fiber that drape over each other and about the pins 414 of the tenter frame. Base fiber 410 is spun from molten resin from one or more rotating or oscillating nozzles 432 above the tenter frame, and allowed to fall loose to the tenter frame, such that in its spun and laid state the fiber is not in tension. The base fiber is sufficiently soft at this point in the process that overlapping layers of coils are draped into one another, with portions of upper coils at a lower elevation than portions of adjacent coils. A useful analogy for visualizing the mass of coils so draped is to consider a single length of rope randomly and loosely draped in overlapping coils onto a level surface. Some of the coils at the edges of the mat of fiber so formed encircle pins 414 of the tenter frame rails. Preferably, at least one base fiber 410 extends the full width of the tenter frame, encircling pins 414 on both sides. The base fiber (or fibers) will primarily form the stretched base of the final product, from which the loop formations extend.

Either during the lay-down of base fiber 410, or immediately thereafter, one or more layers of staple fibers (not shown) are laid upon the mat of the base fiber. These fibers may be blown onto the mat, for instance, in a continuous process during the spinning of base fiber 410, such that staple fibers are deposited between overlapping portions of base fiber 410. In this illustration, the width $W_1$ of the as-laid fiber mat is about 36 to 50 inches, and the staple fibers are only about 4 or 5 inches in length.

Base fiber 410 is subsequently stretched, preferably in two perpendicular directions, by pulling its coils which encircle the tenter frame pins 414. The pulling and stretching is accomplished by the relative motions of the tenter frame pins, both in the machine direction (the ratio of $D_2$ to $D_1$ is about 1.5:1) and in the transverse direction ($W_2$ is about 70 to 100 inches), such that the base fiber is pulled in both directions simultaneously. As the mat is pulled, overlapping coils of the base fiber 410 (or fibers) slide over one another and become entangled with either each other or the staple fibers, forming a random array of spaced apart entanglements 416 connected by taut portions 418 of base fiber 410. Some portions of base fiber 410 remain slack, but the stretching tightens enough portions of the base fiber to form a planar web. At a substantial number of entanglements 418 an extending loop structure (or tree) is formed, consisting primarily of one or more staple fibers drawn up by the forming entanglement, with an occasional loop of base fiber 410. The stretched web is thereafter stabilized in its stretched condition by application of a binder (as described above) or by lamination to a supporting material.

In the continuous monofilament base-forming technique illustrated in FIGS. 13 and 13A, it is important that the unstretched batt be so constructed that a sufficient density of entanglements form upon stretching. In needled batts, entanglements are formed about fiber portions that locally extend perpendicularly to the plane of the batt, having been pushed into and perhaps through the batt by needles. Entanglements can be formed in the continuous monofilament process by several mechanisms. For instance, appropriately layering overlapping coils (or slack sections) of a single base fiber can result in an entanglement upon stretching if top coils are allowed to drape down within two or more lower coils. Two or more base fibers can be spun in a pattern selected to cause the fibers to cross at several points, creating cross-over points at which the fibers pull against each other during stretching. The staple fibers, especially if blown into the batt during the laying of the base fibers, can also form obstructions that result in tightenable entanglements upon stretching. In addition, the spun base fibers may be accelerated into the batt in a manner that causes portions of the base fibers to assume locally perpendicular orientations, extending into the batt between adjacent fibers.

In most cases where significant strength performance is desired, it is preferable to employ non-woven materials formed of staple fibers to take advantage of their drawn, molecular oriented structure, or other fibers of the substantial tenacity. We have found that loops formed of crimped staple fibers work particularly well, as the crimps of the fibers help to hold the loops apart from each other and exposed for engagement, as well as permitting greater hook penetration of the "forest" of loop structures. The crimps can also assist in the formation of the loop structures, as they form snag points for enhancing the entangling of the base fibers.

Inter-fiber friction is known to be important for efficient needling. Because of its higher friction, polyester is considered to be a better fiber material for needling than polyethylene, even though polyethylene can provide a better hand for some applications. For products tightened by stretching rather than hyper-needling, however, lower needling efficiencies can be tolerated, enabling the use of low-friction, good hand materials like polyethylene.

Figure 15:
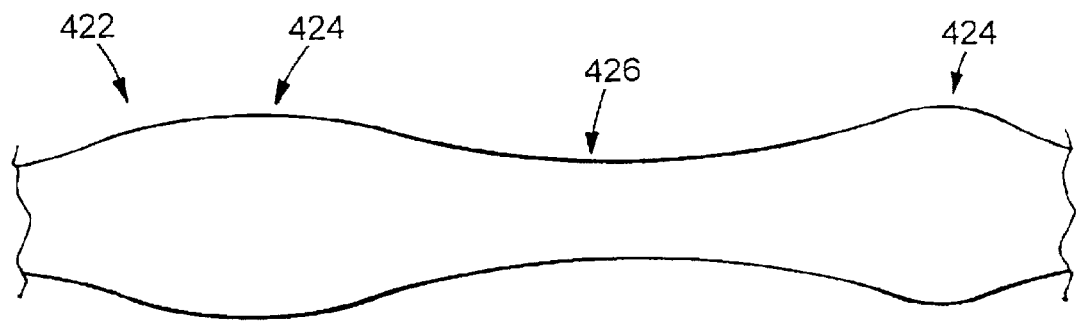
FIG. 15 is an enlarged illustration of a fiber of varying cross-section.

FIG. 15 shows an enlarged portion of a variable thickness staple fiber 422 useful for forming loops. Along its length, the thickness of the fiber undulates to give the fiber an hourglass shape, having alternating thicker regions 424 and thinner regions 426. These thickness variations, which are exaggerated in the figure for illustration, create snag points during entanglement in a similar fashion as do the crimps of crimped fibers.

Besides being useful for loop-forming fibers, crimped or variable thickness fibers are also useful for forming the stretched base web. The-crimps or thickness variations help to entangle base fibers as they slide against one another during tightening. As known in the art of needling, crimps can also improve needling efficiency. In the embodiment illustrated in FIG. 13, the spun base fiber 410 can be effectively "crimped" by subjecting the spun fiber as it leaves its nozzle to a series of transverse air blasts from one or more directions. An hourglass thickness variation can be produced in spun fibers by modulating the ambient air pressure just outside the opening of the nozzle.

Figure 16:
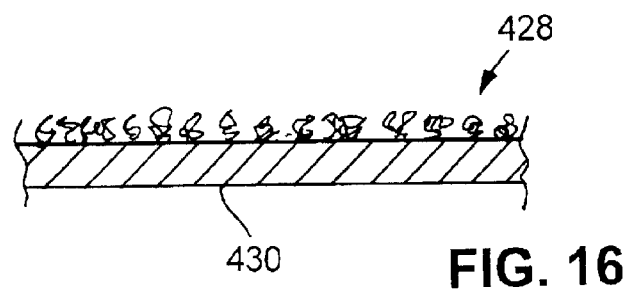
FIG. 16 shows a stretched loop product laminated to a layer of compliant foam.

As mentioned above, in certain applications the stretched web is advantageously secured to a supporting material in its stretched condition. FIG. 16 illustrates a laminate consisting of the stretched web 428 formed by one of the processes described above and a layer of polyurethane foam 430 flame-laminated to its non-loop surface. Ideally, resin of the foam wicks into the entanglements of the base of the loop material to stabilize the material in its stretched condition. However, a small amount of binder may be added to the base of the web before being introduced to the foam, if necessary to maintain the dimensional stability of the stretched web prior to lamination. Such a laminated product is useful, for instance, in medical applications such as for straps and braces which must be loaded directly against the skin. The foam provides necessary comfort, while the loop material provides fastener hook engageability.

Other features and advantages of the invention will be realized, and are within the scope of the following claims.

What is claimed is:

1. A loop component of a hook and loop fastener, the loop component comprising:

a nonwoven body of fibers having a basis weight of less than about 4 ounces per square yard, the fibers forming a sheet-form base containing taut sections of fiber extending within a common plane between tightened knots of fibers, and a great multiplicity of loop formations dispersed across the base, each loop formation having a trunk of fibers drawn together by taut fibers of the base and extending from an associated knot in the common plane of the base, wherein at least some of the fibers comprising the trunk each have a thickness that undulates alone their length, and multiple hook-engageable loops formed of fibers of the trunk and extending from the trunk for engagement by hooks of a mating component.

2. The loop component of claim 1 in which the majority of fibers forming the trunks and hook-engageable loops are crimped.

3. The loop component of claim 1 in which the knots of the base each correspond to an associated previous penetration of the body of fibers by a needle.

4. The loop component of claim 3 in which the body of fibers comprises crimped staple fibers.

5. The loop component of claim 1 in which the fibers comprising the trunks of the loop formations are secured together by a cured binder in interstices within the trunks.

6. The loop component of claim 5 in which the cured binder composes between about 20 and 40 percent of the total weight of the body of fibers.

7. The loop component of claim 1 in which the fibers comprising the trunks of the loop formations are secured together by fused surface portions of at least some of the fibers comprising the trunks.

8. The loop component of claim 1 in which the fibers comprising the trunks of the loop formations are secured together by interlocking crimps of the fibers.

9. The loop component of claim 1 further comprising a resilient layer of foam laminated to the base of the body of fibers.

10. The loop component of claim 1 further comprising a layer of resin laminated to the base of the body of fibers.

11. The loop component of claim 10 in which the resin layer forms hook projections shaped to engage the loops of the component.

12. The loop component of claim 1 having a basis weight of less than about 2 ounces per square yard.

13. The loop component of claim 1 in which the hook-engageable loops extend to an average loop height, measured as the perpendicular distance from the sheet-form base, of between about 0.020 and 0.060 inch.

14. The loop component of claim 13 in which the body of fibers has an overall thickness, defined to include the sheet-form base and a majority of the loops, the average loop height being between about 0.5 and 0.8 times the overall thickness of the body of fibers.

15. The loop component of claim 1 in which the sheet-form base has between about 50 and 1000 tightened knots per square inch of area, from which hook-engageable loop formations extend.

16. The loop component of claim 1 in which the body of fibers is generally composed of fibers having a tenacity of at least 2.8 grams per denier.

17. The loop component of claim 1 having a Gurley stiffness of less than about 300 milligrams.

18. A non-woven loop fabric for engaging hooks in a hook-and-loop fastener, the fabric having a basis weight of less than about 2 ounces per square yard and comprising
a stretched, non-woven mat of fibers entangled at knots therein, the mat having a front side and
free-standing and spaced-apart loop structures extending at least from the front side of the mat from the knots in the mat, said structures defining hook-engageable loops and corresponding associated knots,
the mat being stabilized in a condition of at least 20 percent areal stretch.

19. The loop fabric of claim 18 wherein the mat is stabilized in a condition of at least 50 percent areal stretch.

20. The loop fabric of claim 18 wherein the mat is stabilized in a condition of at least 100 percent areal stretch.

21. The loop fabric of claim 18 wherein at least some of the knots of the mat are secured to resist relative fiber motion therein and further stretching of the fabric.

22. The loop fabric of claim 21 further comprising a binder to secure the fibers of the loop structures at their associated knots.

23. The loop fabric of claim 22 wherein the binder is solidified, fluid-applied binder.

24. The loop fabric of claim 22 comprising between about 20 and 40 percent binder, by weight.

25. The loop fabric of claim 22 wherein the binder is selected from the group consisting of acrylics, urethanes, polyvinyls, formaldehydes, glyoxals and epoxies.

26. The loop fabric of claim 22 wherein the binder comprises a fire-retardant material.

27. The loop fabric of claim 22 wherein the binder comprises polymer filaments entangled among said fibers, said filaments being at least partially melted to encapsulate said knots.

28. The loop fabric of claim 22 wherein the binder forms a backing that is adapted to be welded to a substrate.

29. The loop fabric of claim 18 wherein at least some of the loop structures each comprise multiple loops emanating from a common fiber knot.

30. The loop fabric of claim 18 having an overall thickness, including the mat and a majority of the loop structures, of less than about 0.150 inch.

31. The loop fabric of claim 18 wherein the loops extend to an average loop height from their associated entanglements, measured as the perpendicular distance from the mat, of between about 0.020 and 0.060 inch.

32. The loop fabric of claim 31 wherein the fabric has an overall thickness, including the mat and a majority of the loop structures, and wherein the average loop height is between about 0.5 and 0.6 times the overall thickness of the fabric.

33. The loop fabric of claim 18 having a knot density of between about 50 and 1000 knots per square inch of mat.

34. The loop fabric of claim 33 having a knot density of between about 100 and 600 knots per square inch of mat.

35. The loop fabric of claim 34 having a knot density of between about 150 and 300 knots per square inch of mat.

36. The loop fabric of claim 18 wherein the fibers generally have a tenacity of at least 2.8 grams per denier.

37. The loop fabric of claim 18 wherein the fibers generally have a tenacity of at least 5 grams per denier.

38. The loop fabric of claim 37 wherein the fibers generally have a tenacity of at least 8 grams per denier.

39. The loop fabric of claim 18 wherein the loops of the loop structures extend from the mat to varied heights to form a multi-level arrangement of hook-engageable loops.

40. The loop fabric of claim 18 wherein at least some of the loop structures each comprising
a common, elongated trunk portion extending from the mat from an associated knot and multiple loops extending from the trunk portion.

41. The loop fabric of claim 18 wherein the loop structures generally each comprise three or more hook-engageable loops.

42. The loop fabric of claim 18 wherein the fibers are generally of 15 denier or less.

43. The loop fabric of claim 18 wherein the fibers are generally of 8 denier or less.

44. The loop fabric of claim 18 wherein the fibers are crimped at a crimp density of at least about 7 crimps per inch.

45. The loop fabric of claim 18 wherein the fibers are of a material selected from the group consisting of polyester, polyurethane, polypropylene, polyethylene, nylon, homopolymers, mixtures, copolymers, alloys or coextrusions thereof and natural fibers.

46. The loop fabric of claim 18 having a Gurley stiffness of less than about 300 milligrams.

47. The loop fabric of claim 46 having a Gurley stiffness of less than about 100 milligrams.

48. A loop product for hook-and-loop fastening, comprising a stretched, non-woven fabric of entangled fibers having front and back surfaces, the front surface having exposed, through-forced loops of said fibers extending therefrom capable of being engaged by a hook-type fasteners, and a binder securing the fibers at the back surface of the fabric to resist further elongation of the fabric, and stabilizing the fabric in a state of at least 20 percent areal stretch.

49. A loop product for hook-and-loop fastening, comprising a stretched, non-woven fabric of entangled fibers having front and back surfaces, the front and back surfaces having exposed, through-forced loops of said fibers extending therefrom capable of being engaged by hook-type fasteners, a binder securing the fibers to resist further elongation of the fabric, and stabilizing the fabric in a state of at least 20 percent areal stretch.

* * * * *